US008946284B2

United States Patent
Bristow et al.

(10) Patent No.: US 8,946,284 B2
(45) Date of Patent: Feb. 3, 2015

(54) METHODS AND COMPOSITIONS INVOLVING (S)-BUCINDOLOL

(75) Inventors: Michael R. Bristow, Englewood, CO (US); Jonathan D. Port, Denver, CO (US)

(73) Assignee: Arca Biopharma, Inc., Broomfield, CO (US)

( * ) Notice: Subject to any disclaimer, the term of this patent is extended or adjusted under 35 U.S.C. 154(b) by 288 days.

(21) Appl. No.: 13/056,916

(22) PCT Filed: Jan. 27, 2009

(86) PCT No.: PCT/US2009/032144
§ 371 (c)(1),
(2), (4) Date: May 4, 2011

(87) PCT Pub. No.: WO2010/014263
PCT Pub. Date: Feb. 4, 2010

(65) Prior Publication Data
US 2012/0108617 A1    May 3, 2012

Related U.S. Application Data

(60) Provisional application No. 61/085,586, filed on Aug. 1, 2008.

(51) Int. Cl.
*A61K 31/4045*    (2006.01)
*C07D 209/12*    (2006.01)
*C07D 209/14*    (2006.01)

(52) U.S. Cl.
CPC .................................. *C07D 209/14* (2013.01)
USPC .......................................... 514/415; 548/504

(58) Field of Classification Search
USPC ....................................................... 548/504
See application file for complete search history.

(56) References Cited

U.S. PATENT DOCUMENTS

| | | | | |
|---|---|---|---|---|
| 4,234,595 | A | 11/1980 | Kreighbaum et al. | 514/415 |
| 5,208,233 | A | 5/1993 | Keefer et al. | 514/231.8 |
| 6,358,536 | B1 | 3/2002 | Thomas | 424/608 |
| 6,927,036 | B2 | 8/2005 | Gallop et al. | 435/129 |
| 6,951,860 | B2 | 10/2005 | Mehanna et al. | 514/252.12 |
| 7,052,695 | B2 | 5/2006 | Kalish | 424/178.1 |
| 7,138,430 | B2 | 11/2006 | Garvey | 514/456 |
| 7,155,284 | B1 | 12/2006 | Whitehurst et al. | 607/44 |
| 7,348,319 | B2 | 3/2008 | Hrabie et al. | 514/149 |
| 7,396,829 | B2 | 7/2008 | Garvey et al. | 514/223.2 |
| 7,678,824 | B2 | 3/2010 | Liggett et al. | 514/415 |
| 2002/0077328 | A1 | 6/2002 | Hassan et al. | 514/263.31 |
| 2005/0118286 | A1 | 6/2005 | Suffin et al. | 424/752 |
| 2006/0024365 | A1 | 2/2006 | Vaya et al. | 424/468 |
| 2008/0096982 | A1 | 4/2008 | Liggett et al. | 514/415 |
| 2008/0227844 | A1 | 9/2008 | Liggett et al. | 514/415 |

FOREIGN PATENT DOCUMENTS

| | | |
|---|---|---|
| GB | 2 001 633 | 2/1979 |
| WO | WO 87/03584 | 6/1987 |
| WO | WO 99/20266 | 4/1999 |
| WO | WO 99/67231 | 12/1999 |
| WO | WO 00/21509 | 4/2000 |
| WO | WO 02/05799 | 1/2002 |
| WO | WO 02/41883 | 5/2002 |
| WO | WO 03/092617 | 11/2003 |
| WO | WO 2005/113012 | 12/2005 |
| WO | WO 2006/031955 | 3/2006 |
| WO | WO 2007/098390 | 8/2007 |

OTHER PUBLICATIONS

"Enantiomer." Wikipedia, The Free Encyclopedia. Wikimedia Foundation, Inc. Jul. 22, 2004. Web. Jun. 20, 2008.
Aguilar-Salinas et al., "Characteristics of patients with type 2 diabetes in México: Results from a large population-based nationwide survey," *Diabetes Care*, 26:2021-2026, 2003.
Asano et al., "Bucindolol, a nonselective beta 1- and beta 2-adrenergic receptor antagonist, decreases beta-adrenergic receptor density in cultured embryonic chick cardiac myocyte membranes," *J. Cardiovasc. Pharmacol.*, 37(6):678-91, 2001.
Best Investigators, A Trial of the Beta-Blocker Bucindolol in Patients with Advanced Chronic Heart Failure, *N Engl J Med.*, 344:1659-1667, 2001.
Bhattacharyya and Galluzzo, "Obviousness of Entantiomers after KSR," available online at http://www.law360.com/articles/86436/obviousness-of-enantiomers-after-ksr, Mar. 26, 2009.
Bristow et al., "Beta 1- and beta 2-adrenergic-receptor subpopulations in nonfailing and failing human ventricular myocardium: coupling of both receptor subtypes to muscle contraction and selective beta 1-receptor down-regulation in heart failure ," *Circ. Res.*, 59(3):297-309, 1986.
Bristow et al., "Effect of baseline or changes in adrenergic activity on clinical outcomes in the beta-blocker evaluation of survival trial," *Circulation*, 10(11):1437-42, 2004.
Bristow et al., "Second- and third-generation beta-blocking drugs in chronic heart failure ," *Cardiovasc Drugs Ther.*, Suppl 1:291-6, 1997.

(Continued)

*Primary Examiner* — Shawquia Jackson
(74) *Attorney, Agent, or Firm* — Fulbright & Jaworski LLP

(57) ABSTRACT

Disclosed is bucindolol substantially free of its R-stereoisomer. Also disclosed are pharmaceutical compositions that include bucindolol substantially free of its R-stereoisomer or a pharmaceutically acceptable salt thereof, and a pharmaceutically acceptable carrier. Also disclosed are methods of treating a patient that involve administering to the patient a therapeutically effective amount of a composition of the present invention. Formula (I).

21 Claims, 16 Drawing Sheets

(56) References Cited

OTHER PUBLICATIONS

Bristow et al., "Beta 1- and beta 2-adrenergic receptor-mediated adenylate cyclase stimulation in nonfailing and failing human ventricular myocardium.," *Mol. Pharmacol.*, 35:295-303, 1989.

Bristow et al., "Dose-response of chronic beta-blocker treatment in heart failure from either idiopathic dilated or ischemic cardiomyopathy. Bucindolol Investigators," *Circulation*, 89(4):1632-1642, 1994.

Bristow et al., "The role of third-generation beta-blocking agents in chronic heart failure," *Clin. Cardiol.*, 21(12 Suppl l):13-13, 1998.

Bristow et al. "Selective versus nonselective beta-blockade for heart failure therapy: are there lessons to be learned from the COMET trial?" *J Card Fail.*, 9:444-53, 2003.

Bristow, "Antiadrenergic therapy of chronic heart failure: surprises and new opportunities," *Circulation*, 107:1100-2, 2003.

Bristow, "What type of β-blocker should be sued to treat chronic heart failure?" *Circulation*, 102:484-486, 2000.

Bristow, "β-adrenergic receptor blockade in chronic heart failure," *Circulation*, 10:558-569, 2000.

Brodde et al., "Regional distribution of beta-adrenoceptors in the human heart: coexistence of functional beta 1- and beta 2-adrenoceptors in both atria and ventricles in severe congestive cardiomyopathy," *J. Cardiovasc., Pharmacol.*, 8:1235-1242, 1986.

Brodde et al., "[Importance of beta 2-adrenergic receptors in heart failure]" *Z. Kardiol.*, 81:7178, 1992. (Article in German; English abstract provided).

Campia et al., "Reduced endothelium-dependent and -independent dilation of conductance arteries in African Americans," *J. Am. Coll. Cardiol.*, 40:754-760, 2002.

Carson et al., "Determination of Hospitalization Type by Investigator Case Report Form or Adjudication Committee in a Large Heart Failure Clinical Trial (BEST)," abstract submitted to *HFSA*, 2008.

CIBIS Investigators, "The Cardiac Insufficiency Bisoprolol Study II (CIBIS-II): a randomised trial," *Lancet*, 353(9146):9-13, 1999.

Cohn et al., "Plasma norepinephrine as a guide to prognosis in patients with chronic congestive heart failure," *N. Engl. J. Med.*, 311:819-823, 1984.

Danielewicz and Kemp, "Absolute configuration by asymmetric synthesis of (+)-1-(4-acetamidophenoxy)-3-(isopropylamino)-propan-z-ol (practolol).," *J. Med. Chem.*, 16:168-169, 1973.

Database CA [Online] Chemical Abstracts Service, Columbus, Ohio, US; Registry No. 91548-61-7 of Bucinolol S-isomer 1985, Weyl, J. D. et al., "Differential cardioprotective properties of the L- and D-enantiomers of bucindolol in a canine model of heart failure," XP002524176, retrieved from STN Database accession No. 1985:481463. Abstract.

De Amici et al., "beta-3-Adrenergic receptor ligands: insight into structure-activity relationships using Monte-Carlo conformational analysis in water," *Tetrahedron*, 57(9):1849-1855, 2001.

Dohlman et al., "Model systems for the study of seven-transmembrane-segment receptors," *Annu. Rev. Biochem.*, 60:653-688, 1991.

Domanski et al., "The effect of diabetes on outcomes of patients with advanced heart failure in the BEST trial," *J. Am. Coll. Cardiol.*, 42:914-922, 2003.

Eichhorn and Bristow, "Medical therapy can improve the biological properties of the chronically failing heart. A new era in the treatment of heart failure," *Circulation*, 94(9):2285-96, 1996.

Gavai et al., "Discovery of novel 1-arylemthyl pyrrolidin-2-yl ethanol amines as calcium-sensing receptor antagonists," *Bioogranic & Medicinal Chemistry Letters*, 15(24):5478-5482, 2005.

Gilbert et al., "Long-term beta-blocker vasodilator therapy improves cardiac function in idiopathic dilated cardiomyopathy: a double-blind, randomized study of bucindolol versus placebo,"*Am J Med.*, 88:223-229, 1990.

Harrison, "Cellular and molecular mechanisms of endothelial cell dysfunction," *J. Clin. Invest.*, 100:2153-2157, 1997.

Hershberger et al., "Mechanism of action of bucindolol in human ventricular myocardium ,"*J. Cardiovasc Pharmacol.*, 15(6):959-67, 1990.

Huertas-Vazquez et al., "Familial combined hyperlipidemia in Mexicans: association with upstream transcription factor 1 and linkage on chromosome 16q24.1,"*Arterioscler. Thromb. Vasc. Biol.*, 25:1985-1991, 2005.

Hunt et al., "All-cause and cardiovascular mortality among diabetic participants in the San Antonio Heart Study: evidence against the "Hispanic Paradox"" *Diabetes Care*, 25(9):1557-1563, 2002.

Kalinowski et al., "Race-specific differences in endothelial function: predisposition of African Americans to vascular diseases," *Circulation*, 109:2511-2517, 2004.

Kamath et al., "Pharmacophores of the dual acting alpha,beta-blockers as deduced from molecular dynamics simulations," *Journal of Bioscience*, 2195):599-611, 1996.

Kolomiets et al., "Kinetic resolution of secondary alcohols and aurins by means of S-(-31 )-α-Phenylethyl Isocyanate," *Journal of Organic Chemistry of the USSR*, a translation of *Zhurnal Organicheskoi Khimii*, vol. 16, No. 5, Part 1, pp. 854-857 (English), 1980.

Levin et al., "The myocardium-protective Gly-49 variant of the beta 1-adrenergic receptor exhibits constitutive activity and increased desensitization and down-regulation," *J Biol. Chem.*, 277(34):30429-30435, 2002.

Liggett, "Beta-adrenergic receptors in the failing heart: the good, the bad, and the unknown," *J. Clin. Invest.*, 107:947-948, 2001.

Liggett et al., "A polymorphism within a conserved beta(1)-adrenergic receptor motif alters cardiac function and beta-blocker response in human heart failure," *Proc Natl Acad Sci USA.*, 103:11288-11293, 2006.

Liggett et al., "Pharmacology and molecular biology of adrenergic receptors," In: Baillière's Clinical Endocrinology and Metabolism, Bouloux (Ed.), W. B. Sounders, London, 1993. vol. 7, No. 2, pp. 279-306.

Lindenfeld et al., "Ischemic cardiomyopathy response to bucindolol may be differentially influced by beta-1 389 Arg/Gly and alpha-2c genotypes," abstract submitted to *HFSA*, 2008.

Lindenfield et al., "Different patterns of LVEF/remodeling and clinical endpoint effects for bucindolol in beta-1-AR 389 Arg/Gly genotypes," abstract submitted to *HFSA*, 2008.

Lowes et al., "Myocardial gene expression in dilated cardiomyopathy treated with beta-blocking agents," *N Engl J Med.*, 346(18):1357-65, 2002.

Lowes et al., "Differential effects of β-blocking agents on adrenergic activity," *Circulation*, 102(18), Supplement II, pp. II628-II629, 2000.

Lowes, "Inotropes in the Beta-Blocker era," *Clin. Cardiol.*, 23(Suppl. III), III-11-III-16, 2000.

Mason et al., "A gain-of-function polymorphism in a G-protein coupling domain of the human beta1-adrenergic receptor," *The Journal of Biological Chemistry*, 274:12670-4, 1999.

Mason et al., "Effect of the beta3-receptor antagonist SR59230A on bucindolol-induced release of nitric oxide and peroxynitrite from human endothelium," abstract submitted to *HFSA*, 2008.

Mason et al., "Effects of bucindolol enantiomers on nitric oxide and peroxynitrite release from endothelial cells in ethnic populations," abstract submitted to *HFSA*, 2008.

Mehvar and Brocks, "Seterospecific pharmacokinetics and phyarmacodynamics of beta-adrenergic blockers in humans," *J. Pharm. Pharmaceut. Sci.*, 4(2):185-200, 2001.

MERIT-HF Study Group, 1999.

O'Connor et al., Additive effects of beta-1 389 Arg/Gly alpha-2c Wt/Del genotype combinations on adjudicated hospitalizations and death in the beta-blocker evaluation of survival trial (BEST), abstract submitted to *HFSA*, 2008.

Packer et al., "Effect of carvedilol on survival in severe chronic heart failure," *The New England Journal of Medicine*, 344(22):1651-1658, 2001.

Paniagua et al., "Role of endothelial nitric oxide in shear stress-induced vasodilation of human microvasculature: diminished activity in hypertensive and hypercholesterolemic patients," *Circulation*, 103:1752-1758, 2001.

Panza et al., "Abnormal endothelium-dependent vascular relaxation in patients with essential hypertension," *N. Engl. J. Med.*, 323:22-27, 1990.

(56) References Cited

OTHER PUBLICATIONS

PCT International Search Report and Written Opinion issued in International application No. PCT/US2009-032144, dated Oct. 20, 2009.
PCT Invitation to Pay Additional Fees issued in International application No. PCT/US2009-032144, dated Jan. 27, 2009.
Rathz et al., "Amino acid 49 polymorphisms of the human beta1-adrenergic receptor affect agonist-promoted trafficking," *J Cardiovasc Pharmacol.*, 39(2):155-60, 2002.
Sederberg et al., "Bucindolol has nointrinsic sympathomimetic activity (ISA) in the nonfailing human ventricular preparations," *J. Am. Coll. Cardiol.* 35(2) 207A, 2000.
Siebert et al., "Sterochemical comparison of nebivolol with other beta-blockers," *Chirality*, 20(2):103-109, 2007.
Stein et al., "Vasodilation in black Americans: attenuated nitric oxide-mediated responses," *Clin. Pharmacol. Ther.*, 62:436-443, 1997.
Stephen, "Cardiac failure with propranolol," *Br Med J.*, 2(5602):428, 1968.
Strosberg, "Structure and function of the beta 3-adrenergic receptor," *Annu. Rev. Pharmacol. Toxicol.*, 37:421-450, 1997.
Taddei et al., "Vasodilation to acetylcholine in primary and secondary forms of human hypertension," *Hypertension*, 21:929-933, 1993.
Walsh et al., "Human Myocardial b1 389 Arg/Arg Adrenergic Receptors Exhibit a Propensity for Constitutively Active, High Affinity Agonist Binding and Are Selectively Inactivated by Bucindolol," abstracted submitted to *HFSA*, 2008.
Weyl et al., "Differential cardioprotective properties of the L- and D-enantimoers of bucindolol in a canine model of heart failure," *Archvies Internationales de Pharmacodynamie et de Therapie*, 275(1):4-12, 1985.
Zhu et al., "Dual modulation of cell survival and cell death by beta(2)-adrenergic signaling in adult mouse cardiac myocytes," *Proc. Natl. Acad. Sci. USA*, 98(4):1607-12, 2001.
Zolty et al., "Beta-1 adrenergic polymorphisms alter myocardial gene expression in heart failure," *HFSA*, 2008.

METHODS AND COMPOSITIONS INVOLVING (S)-BUCINDOLOL

The present application is a national phase application under 35 U.S.C. §371 of International Application No. PCT/US2009/032144 filed Jan. 27, 2009, which claims the benefit of priority to U.S. Provisional Patent Application Ser. No. 61/085,586, filed Aug. 1, 2008, which is hereby incorporated by reference in its entirety.

BACKGROUND OF THE INVENTION

1. Field of the Invention

The present invention relates generally to the fields of pharmacology and clinical medicine. More specifically, the present invention is directed to pharmaceutical compositions and methods for treatment of disease in humans that concern S-bucindolol.

2. Description of Related Art

The human endothelium has an essential role in regulating arterial blood flow and preserving normal vascular physiology. Important activities of the endothelium are mediated by the production of signaling molecules, especially nitric oxide (NO). Endothelial dysfunction, on the other hand, is linked to atherosclerosis and its clinical manifestations (coronary artery disease, heart failure) (Harrison et al., 1987; Liao, 1998; Oemar et al., 1998). Key risk factors for atherosclerosis, including dyslipidemia, smoking and diabetes, can be specifically linked to abnormalities in NO-mediated endothelial dilation (Harrison et al., 1987; Liao, 1998; Oemar et al., 1998). In addition, a reduction in NO bioavailability contributes to elevated vascular resistance and loss of sensitivity to stimuli of vasodilation, hallmark features of hypertension (Paniagua et al., 2001; Panza et al., 1990; Taddei et al., 1993).

Beyond vasodilation, NO has well-characterized vascular benefits, including inhibition of smooth muscle cell proliferation and migration, adhesion of leukocytes to the endothelium, and platelet aggregation (Harrison, 1997). In patients at higher risk for cardiovascular disease and its clinical consequences (e.g., African Americans), there is also evidence for reduced NO-mediated vasodilation associated with increased superoxide generation in endothelial cells (Campia et al., 2002; Kalinowski et al., 2004; Stein et al., 1997). Thus, agents that directly stimulate NO release may have important therapeutic advantages in the prevention and treatment of cardiovascular disease.

Hispanics are the largest and fastest-growing minority group in the United States, and Mexican Americans are the largest sub-group of Hispanics. Epidemiologic studies indicate that Mexicans have higher rates of coronary heart disease (CHD) risk equivalents, including type 2 diabetes mellitus, metabolic syndrome and some primary forms of dyslipidemia (Stem et al., 1991; Aguilar-Salinas et al., 2001; Aguilar-Salinas et al., 2003). By the age of 50, epidemiologic studies indicate that 28% of men and 21% of women in Mexico already exhibit some form of dyslipidemia (Aguilar-Salinas et al., 2001). In the San Antonio Heart Study, it was reported that after adjusting for age and gender, U.S.-born Mexican Americans were 1.4 times as likely to die of cardiovascular (CV) disease as non-Hispanic whites (Hunt et al., 2002). For cardiovascular disease, U.S.-born Mexican Americans were 1.7 times more likely to die from CVD and 1.9 times more likely to die from CHD than non-Hispanic whites (Hunt et al., 2002). To understand the basis for this enhanced risk, a recent study has identified genetic variants that confer higher susceptibility to dyslipidemia, but more studies are needed in this area (Aguilar-Salinas et al., 2003; Huerta-Vazquez et al., 2005). There are also well known environmental factors that contribute to higher risk in individual Mexican Americans, including a high-fat and high-calorie diet, tobacco use, alcohol consumption and sedentary lifestyle.

Hypertension is a risk factor that is less likely treated and controlled among Hispanics, as compared to the overall U.S. population. This was a key finding from the National Health and Nutrition Examination Surveys (NHANES) for 1999-2002. This report has identified racial/ethnic disparities in the awareness of, treatment for, and control of hypertension. NHANES is a stratified, multistage probability sample of the civilian, non-institutionalized U.S. population. During 1999-2002, the age-adjusted prevalence of hypertension in the study population was 28.6% (CI=26.8%-30.4%). The prevalence of hypertension increased with age, as expected, and was higher among women than men. Among adults with hypertension, the proportion aware of having this condition was 70.3% among non-Hispanic blacks, 62.9% among non-Hispanic whites, but only 49.8% among Mexican Americans. The age-adjusted proportion that reported treatment was 55.4% among non-Hispanic blacks, 48.6% among non-Hispanic whites, and only 34.9% among Mexican Americans. Only 29% of U.S. adults with hypertension had controlled BP levels (<140/90 mmHg). The proportion with controlled BP was similar among non-Hispanic blacks (29.8%) and non-Hispanic whites (29.8%) but substantially lower among Mexican Americans (17.3%). These findings indicate the challenge of effectively treating and controlling hypertension in the rapidly growing Hispanic and Mexican American population.

While epidemiologic studies indicate a higher risk of CV disease and lower BP control among Mexican Americans, the underlying pathophysiology is not well understood. Studies in other high-risk populations, such as African Americans, indicate that the higher risk is related to decreased responsiveness of conductance vessels to both endogenous and exogenous stimulants of NO, as compared with age-matched whites (Campia et al., 2002). To understand the basis for this difference, it was reported that there is lower bioavailability of NO from endothelium of black Americans, despite much higher levels of endothelial-dependent NO synthase (eNOS) (Kalinowski et al., 2004). The cellular basis for this paradox was the finding that excessive $O_2^-$ generation by NAD(P)H-oxidase and uncoupled eNOS resulted in the loss of functional NO due to its reactivity with $O_2^-$, resulting in peroxynitrite ($ONOO^-$) formation, a potent oxidant with the capacity to produce adverse biological effects (Kalinowski et al., 2004).

Thus, there is the need for improved therapy of hypertension and CV disease, particularly among racial groups where there is a high prevalence of these diseases.

SUMMARY OF THE INVENTION

The present invention relates to the finding that the S-stereoisomer of bucindolol (S-bucindolol) has a greater capacity of inducing cells to generate NO compared to bucindolol racemate while simultaneously reducing $ONOO^-$ production. The present invention is also related to the finding that S-bucindolol demonstrates particularly favorable activity in racial groups including African Americans, Mexican Americans, and non-Hispanic whites.

Certain embodiments of the present invention concern methods and compositions involving bucindolol (2-(3-(1-(1H-indol-3-yl)-2-methylpropan-2-ylamino)-2-hydroxypropoxy)benzonitrile), substantially free of its R-stereoisomer. A composition is "substantially free" of R-bucindolol if it includes a mixture of S-bucindolol and (optinally) R-bucindolol wherein the weight of R-bucinolol, if present, is no more than about 20% of the total weight of S-bucindolol and R-bucindolol in the composition. In some embodiments, the composition may contain no more than about 20, 19, 18, 17, 16, 15, 14, 13, 12, 11, 10, 9, 8, 7, 6, 5, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or 1.0% or any range derivable therein by weight of R-bucindolol relative to the total weight of S-bucindolol and R-bucindolol in the composition. In some particular embodiments, the composition that is substantially free of R-bucindolol contains no more than about 20% by weight of R-bucindolol relative to the total weight of S-bucindolol and R-bucindolol in the composition. In more particular embodiments, the composition contains no more than about 10% by weight of R-bucindolol relative to the total weight of S-bucindolol and R-bucindolol in the composition. In more particular embodiments, the inventive composition contains no more than about 10% of R-bucindolol relative to the total weight of S-bucindolol and R-bucindolol in the composition. In even more particular embodiments, the inventive composition contains no more than about 1% of R-bucindolol relative to the total weight of S-bucindolol and R-bucindolol in the composition.

In some embodiments of the invention, it is contemplated that bucindolol includes pharmaceutically acceptable salts of bucindolol. Thus, for example, a composition comprising S-bucindolol may include a pharmaceutically acceptable salt of S-bucindolol. In particular embodiments of the present invention, embodiments include bucindolol or pharmaceutical compositions of bucindolol that do not include any pharmaceutically acceptable salts of bucindolol.

In certain embodiments of the present invention, the bucindolol in the composition is substantially purified. "Substantially purified" as set forth herein refers to a composition comprising bucindolol wherein the composition includes at least about 80% S-bucindolol. In some embodiments, the composition includes at least about 81, 82, 83, 84, 85, 86, 87, 88, 89, 90, 91, 92, 93, 94, 95, 96, 97, 98, 99, 99.2, 99.2, 99.3, 99.4, 99.5, 99.6, 99.7, 99.8, or 99.9% by weight of S-bucindolol relative to total bucindolol in the composition.

The pharmaceutical composition may optionally include one or more additional pharmaceutical agents. Any pharmaceutical agent is contemplated for inclusion in the compositions. Examples of specific agents are set forth in the specification below. In some embodiments, the pharmaceutical agent is an agent that can be applied in the treatment or prevention of a cardiovascular disease, a neurological disease, an infectious disease, an inflammatory disease, a neoplasm, a gastrointestinal disease, a genitourinary disease, a pulmonary disease, or an immune disease. In some embodiments the pharmaceutical agent is an additional β-adrenergic receptor blocker. Non-limiting examples of beta-adrenergic receptor blockers include AC 623, acebutolol, aiprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrocholoride, butofilolol, carazolol, carteolol, carvedilol, celiprolol, cetamolol, cloranolol, dilevalol, esmolol, indenolol, labetalol, landiolol, levobunolol, mepindolol, metipranolol, metoprolol, moprolol, nadolol, nadoxolol, nebivolol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

In other embodiments, the composition may include a nitric oxide (NO) enhancing agent. Examples of NO enhancing agents are well known to those of ordinary skill in the art. Examples of such agents include a RAS inhibitor, a statin, a PDE5 inhibitor, a NO-conjugated drug, or a diazeniumdiolate. Non-limiting examples of RAS inhibitors include captopril, cilazapril, enalapril, fosinopril, lisinopril, quinapril, ramapril, zofenopril, candesartan cilexetil, eprosartan, irbesartan, losartan, tasosartan, tehnisartan, and valsartan, or a pharmaceutically acceptable salt thereof. Non-limiting examples of statins include atorvastatin, fluvastatin, lovastatin, pravastatin, rosuvastatin calcium, and simvastatin. Non-limiting examples of NO-conjugated drugs include S—NO-glutathione, NO-naproxen, NO-aspirin, NO-ibuprofen, NO-Diclofenac, NO-Flurbiprofen, NO-Ketoprofen, NO-releasing compound 7, NO-releasing compound 5, NO-releasing compound 12, or NO-releasing compound 18. Other examples of NO enhancing agents include L-arginine, arginine alpha-ketoglutarate, GEA 3175, sodium nitroprusside, glyceryl trinitrate, S-nitroso-N-acetyl-penicillamine, nitroglycerin, and diethylamine NONOate. Information concerning NO generating compounds for treating hypertension and atherosclerosis can be found in U.S. Pat. Nos. 7,396,829, 7,348,319, 7,155,284, 7,052,695, 6,358,536, and 5,208,233, each of which is herein specifically incorporated by reference. Information regarding nebivolol as an NO-enhancing agent can be found in U.S. Pat. No. 7,138,430, herein specifically incorporated by reference.

The invention also concerns methods of treating a patient involving administering to a patient a therapeutically effective amount of a composition comprising bucindolol wherein the composition is substantially free of the R-stereoisomer of bucindolol. The composition can be any of those compositions set forth above.

In certain embodiments, the patient self-identifies as a Caucasian. In more particular embodiments, the patient self-identifies as a non-Hispanic white. In other embodiments, the patient self-identifies as an individual of African descent. In still further embodiments, the patient self-identifies as a Hispanic. In more particular embodiments, the patient self-identifies as a Mexican American. In some embodiments the patient has a disease or condition such that the patient is in need of a NO enhancing agent. For example, the patient may have a headache, hypoxic respiratory failure, pulmonary hypertension, right ventricular heart failure, congestive heart failure, respiratory distress syndrome, impotence, hypertension, angina, myocardial infarction, or cardiac arrhythmia.

In some embodiments, the patient is in need of a beta-blocker. For example, the patient may be a patient in need of treatment or prevention of hypertension, angina, myocardial infarction, mitral valve prolapse, cardiac arrhythmia, congestive heart failure, hypertrophic obstructive cardiomyopathy, acute dissecting aortic aneurysm, portal hypertension, anxiety disorder, glaucoma, migraine headache, migraine prophylaxis, tremor due to anxiety, tremor due to hyperthyroidism, essential tremor, pheochromocytoma, or hyperhidrosis.

The method may optionally involve administering to the patient a secondary form of therapy. The secondary form of therapy may be any type of therapy. For example, the secondary form of therapy may be a pharmaceutical agent or a surgical procedure. Non-limiting examples of surgical procedures include angioplasty, valve replacement surgery, heart transplant, coronary artery bypass grafting, and peripheral vascular surgery. The secondary therapy may be administered prior to, concurrently with, or following administration of the therapeutic compositions set forth herein. In particular embodiments, the secondary therapy is a pharmaceutical agent. The pharmaceutical agent may be administered separately from the composition of the present invention, or may be included as a component of a composition as set forth herein. Examples of such pharmaceutical agents are set forth above and elsewhere in this specification.

Administration of the pharmaceutical compositions set forth herein may be by any method known to those of ordinary skill in the art. Examples include, but are not limited to, oral, intravenous, intramuscular, intra-arterial, intramedullary, intrathecal, intraventricular, intradermal, intratracheal, intravesicular, intraocular, transdermal, subcutaneous, intraperitoneal, intranasal, enteral, topical, sublingual, or rectal administration. Further details on techniques for formulation and administration may be found in the specification below.

In some embodiments, the method further includes contacting the patient with a medical device that includes S-bucindolol. For example, the medical device may include a coating that includes S-bucindolol, a matrix that includes S-bucindolol, or a reservoir that includes a therapeutic composition as set forth above. The device may be inserted into the patient temporarily or implanted in the patient or placed on a body surface of the patient. Examples of such body surfaces include skin surfaces or mucosal surfaces.

The medical device may be any medical device known to those of ordinary skill in the art. Non-limiting examples of such medical devices include a stent, a graft, a heart valve, a filter, a catheter, a coil, a mesh repair material, a plate, a rod, a screw, or a suture.

The present invention also concerns methods of increasing the capacity of a cell to generate NO, involving contacting the cell with a composition that includes bucindolol substantially free of its R-stereoisomer or a pharmaceutically acceptable salt thereof, and a pharmaceutically acceptable carrier. The cell may be any type of cell. In particular embodiments the cell is an endothelial cell, an epithelial cell, or a stem cell. In certain embodiments, the cell is a cell that is in a patient or an animal. Non-limiting examples of animals include a mouse, a rat, a rabbit, a cat, a dog, a horse, a sheep, a goat, a cow, or a primate.

The invention also concerns medical devices that include a coating, a matrix, or a chamber, wherein the coating, matrix, or chamber includes bucindolol substantially free of the R-stereoisomer. Non-limiting examples of such medical devices include a stent, a graft, a heart valve, a filter, a catheter, a coil, a mesh repair material, a plate, a rod, a screw, and a suture. An example of a type of filter is an inferior vena caval filter. An example of a type of catheter is a drug infusion catheter. An example of a type of coil is an embolic coil.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
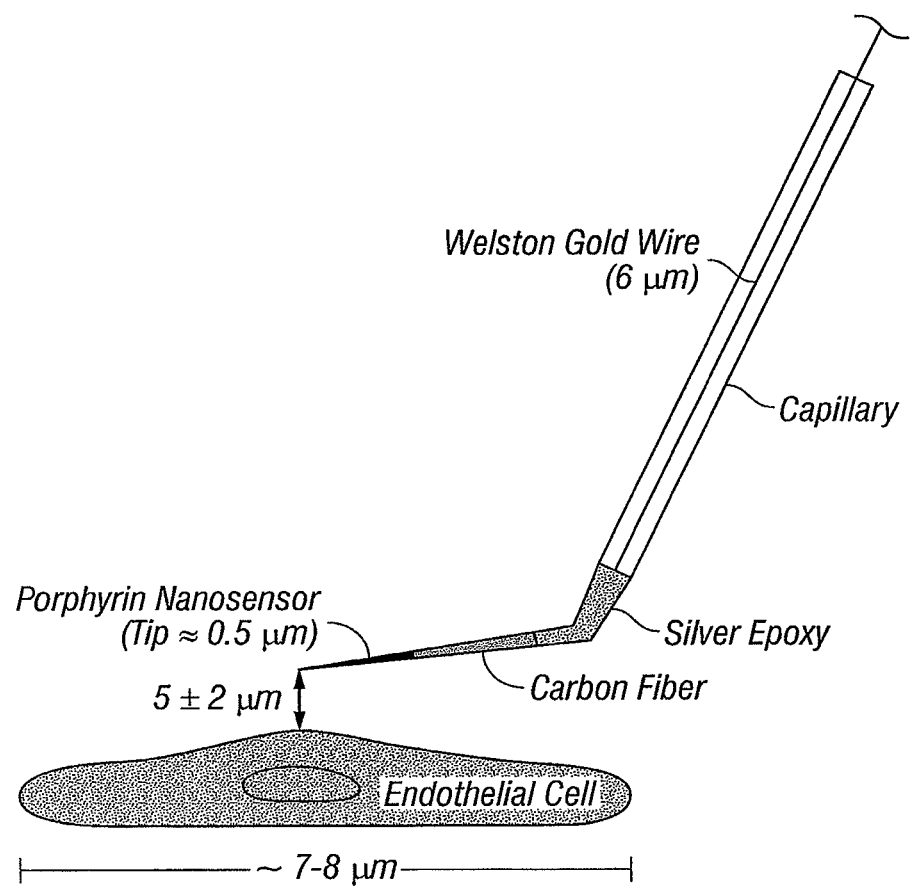
FIG. 1. Schematic diagram of a NO nanosensor placed in close proximity to the surface of a single endothelial cell. The nanosensor measures the levels of NO, $O_2^-$, and $ONOO^-$ from the intact endothelium in real time. The sensors are made by depositing a sensing material on the tip of carbon fiber with a diameter of about 0.5 μm. The fibers are sealed with nonconductive epoxy and electrically connected to wires (gold, copper) with dconductive silver epoxy.

Bucindolol is a nonselective β-blocking agent with mild vasodilatory properties. The present invention is in part based on the finding that the mechanism of vasodilation with bucindolol involves endothelial-dependent nitric oxide (NO) release, and that it is effective in higher risk racial groups, such as African Americans and Mexican Americans. In this regard, the inventors examined the effects of bucindolol and its separate enantiomers on endothelial-dependent NO and nitroxidative stress (peroxynitrite) release in cells from healthy white, African American and Mexican American donors. The effects of bucindolol and its enantiomers were compared to another $\beta_1$-selective antagonist, atenolol. It was found that bucindolol had a dual effect on endothelial function by increasing the capacity of cells to generate NO while simultaneously reducing ONOO⁻ production in a stereoselective manner. The favorable activity of bucindolol on the NO/ONOO⁻ ratio was significant and highly dose-dependent in three different racial groups, including African Americans, Mexican Americans and non-Hispanic whites. The activity of (S)-bucindolol was superior to bucindolol racemate but not reproduced by atenolol under identical conditions.

A. BETA BLOCKERS AND BUCINDOLOL

1. β-Blockers

Treatment for heart failure has involved targeting adrenergic receptors (AR). There are at least nine sub-types of adrenergic receptors (Dohlman et al., 1991; and Liggett et al., 1993), of which at least three sub-types are β-adrenergic receptors.

The $\beta_1$ adrenergic receptor ($\beta_1$AR) is the principle subtype expressed on cardiac myocytes. The human heart expresses both the $\beta_1$AR and the $\beta_2$AR subtypes (Bristow et al, 1986; Bristow et al., 1988). Each receptor mediates positive inotropic and chronotropic responses to endogenous catecholamines and exogenously administered agonists (Bristow et al., 1986; Brodde et al., 1986; Brodde et al., 1992).

The $\beta_1$AR triggers the heart's contractile response when activated, as it is by norepinephrine. In addition, the $\beta_1$ receptor has a central role in the progression of cardiomyopathy and other disease pathways. Increased activation of this receptor and its associated myopathic and arrhythmic pathways plays a major role in the natural history of heart failure. Once the cardiomyopathic process has begun, chronic activation of $\beta_1$-adrenergic receptors can accelerate disease progression, as the failing heart tries to compensate for its impaired functioning by releasing more norepinephrine and increasing $\beta_1$-receptor signaling. The theory of β-receptor blockade rests in part on counteracting this cardiomyopathic pathway by blocking the $\beta_1$-receptor and reducing norepinephrine signaling.

The $\beta_1$ adrenergic receptor has been cloned and sequenced (Frielle et al., 1987). The gene has been localized to chromosome q24-q26 of chromosome 10 (Yang-Feng et al., 1990). The human $\beta_1$AR has a deduced amino acid sequence of 477 amino acids.

At coding nucleotide position 1165 of the $\beta_1$AR gene, either cytosine or guanine can be found in the human population, which results in either Arg or Gly being encoded at amino acid position 389 (Mason et al., 1999). This position is within an intracellular domain of the receptor that is involved with coupling to the stimulatory G-protein, Gs. In fibroblasts transfected to express equal levels of the two receptors, the $\beta_1$-Arg389 receptor display substantially greater stimulation of adenylyl cyclase compared to $\beta_1$-Gly389 (Mason et al., 1999). A less common polymorphism of the $\beta_1$AR, Gly49, has also been identified but there are discrepant reports as to its functional implications (Rathz et al., 2002; Levin et al., 2002).

The $\beta_1$-AR 389Arg/Arg polymorphism is actually the most prevalent form of the $\beta_1$ adrenergic receptor and is present in about 50% of the U.S. population (slightly less in African-Americans). The other variant of this receptor has a glycine (Gly) at the 389 position and is considered the wild type only because it was cloned first. Liu et al. (2003) report finding that a greater response (in terms of changes in heart rate) to metoprolol was associated with Arg389 compared to Gly389.

While $\beta_1$ agonists such as dobutamine, are used for treating acute deterioration of patients with failing ventricular function, prolonged exposure of the heart from administered agonists, or the elevated endogenous catecholamine agonists produced by the body, leads to worsening heart failure. Indeed $\beta_1$AR and $\beta_2$AR become desensitized in heart failure, which is thought to be a mechanism of self-protection against the high levels of catecholamines that exist in heart failure. The administration of $\beta$ antagonists can improve ventricular function and clinical outcomes, presumably by blocking these deleterious effects of catecholamines. And indeed, cardiac $\beta$AR expression and function improve during $\beta$ blockade treatment of heart failure. The vast majority of the deleterious effects of catecholamines, and the success of $\beta$ blocker therapy is due to variants of the $\beta_1$AR subtype. (Zhu et al., 2001; and Bristow et al., 2003).

$\beta$-adrenergic receptor antagonists (also termed $\beta$-blockers) have emerged as a major treatment modality in chronic heart failure. Initially these agents were thought to be contraindicated in heart failure, since increased adrenergic drive was thought to be critical for supporting the failing heart. In fact, in early experience with the $1^{st}$ generation compound propranolol, administration of standard doses was frequently associated with worsening of heart failure (Stephen, 1968). However, using low starting doses and slow up-titration, $2^{nd}$ generation (selective $\beta_1$-blockers) or $3^{rd}$ generation (nonselective $\beta$-blocker-vasodilators) generation compounds have been shown to reverse contractile dysfunction as well as structural and molecular remodeling, and to improve heart failure morbidity and mortality (Bristow, 2000); CIBIS-II Investigators and Committees. The cardiac insufficiency bisoprolol study II: a (CIBIS-II, 1999); MERIT-HF Study Group. Effect of metoprolol CR/XL in chronic heart failure: Metoprolol CR/XL Randomized Intervention Trial in Congestive Heart Failure (MERIT-HF, 1999). Packer et al. (2001); BEST Trial Investigators, (2001); Lowes et al., 2002). In part, these beneficial effects are thought to be due to a protection of the failing heart, which has limited metabolic and physiologic reserves, from persistent adverse biological effects mediated by elevated norepinephrine levels found in the syndrome (Bristow, 2000; Cohn et al., 1984; and Liggett, 2001). In addition, $\beta$-blockers have been shown to partially reverse the molecular phenotype of heart failure (Lowes et al., 2002), so these agents are capable of both preventing and reversing progressive myocardial failure and remodeling Eichhorn and Bristow, Circulation 1996).

Bucindolol and metoprolol have some notable differences in their pharmacologic properties (Bristow, 2000; and Bristow et al., 1997). In particular, bucindolol lowers norepinephrine, dilates the peripheral vasculature, and more potently blocks the human $\beta_1$-adrenergic receptor.

While a common pharmacologic property of all $\beta$-blocking agents that have been used to treat HF is that they block the $\beta_1$AR, which in the failing human heart has been estimated to transduce up to approximately 90% of the pathologic adrenergic stimulation (Zhu et al., 2001; and Bristow et al., 2003), the available $\beta$-blockers have a number of distinguishing properties including $\beta$AR-subtype selectivity, affinity for $\alpha_1$AR, partial agonist activity, sympatholysis (Bristow et al., 2004) and vasodilation (Bristow, 2000; and Bristow et al., 1997).

$\beta$-blockers have significant structural differences. Moreover, they have different pharmacological properties. Carvedilol, for instance, is an efficient $\beta_1$-AR and $\beta_2$-AR blocker, as well as an $\alpha_1$-AR blocker. In contrast, bucindolol is a weak $\alpha_1$-AR blocker, and metoprolol and bisoprolol do not block $\alpha_1$-AR at all. Significantly, bucindolol is unique among $\beta$-blockers in its sympatholytic properties, in contrast to carvedilol, metoprolol, and bisoprolol, which have no such properties. Compared to other $\beta$-blocking agents bucindolol uniquely lowers systemic norepinephrine levels (Lowes et al., 2000; Bristow et al., 1997; BEST NEJM, Bristow, 2004), and is a full agonist for the $\beta_3$-adrenergic receptor (Strosberg, 1997).

2. Bucindolol

Bucindolol is a 3rd generation, $\beta$-blocker-vasodilator with the chemical name and structure of (2-{2-hydroxy-3 {{2-(3-indolyl)-1,1-dimethylethyl}amino}propoxy}-benzonitrile hydrochloride). It was first developed for treatment of hypertension, and subsequently for the treatment of heart failure. Because of its low inverse-agonist and vasodilator properties the nonselective $\beta$-blockade of bucindolol is relatively well tolerated by heart failure patients, and in part for this reason in 1994 bucindolol was selected by the NIH and VA Cooperative Clinical Trials Group to test the hypothesis that a $\beta$-blocker could reduce mortality in advanced heart failure. The test of this hypothesis was the BEST Trial, which was conducted between May 31, 1995 and Jul. 29, 1999.

The Beta-blocker Evaluation of Survival Trial ("BEST") was stopped prematurely on recommendation of the Data and Safety Monitoring Committee, at a time when the hazard ratio for the primary endpoint of all-cause mortality was apparently 0.90 (C.I.s 0.78-1.02) (BEST Investigators, 2001; Domanski et al., 2003). However, the results for the entire BEST cohort were positive for the high order secondary endpoint of mortality or heart failure hospitalization, which was reduced by bucindolol by 19% with a p-value of <0.0001 (Domanski et al., 2003). This endpoint is in fact increasingly viewed as the preferred primary endpoint for HF pivotal trials.

The reasons why BEST was stopped were 1) confirmation by BEST Trial data generated in Class III, non-Black patients of the then recently published information from CIBIS-II (CIBIS Investigators, 1999) and MERIT-HF (MERIT-HF Study Group, 1999) trials that these types of heart failure patients have a substantial survival benefit from β-blockade, 2) increasing loss of equipoise among investigators, who believed that the efficacy of β-blockade in heart failure had been demonstrated, and 3) inefficacy and trends toward adverse events in subgroups (Class IV and Blacks) that had not been previously investigated in β-blocker heart failure trials. Further development of bucindolol was then abandoned because it was not clear bucindolol could be successfully marketed, even if approved.

Therefore, in this large survival trial in which the end point evaluation was overall survival, the BEST clinical trial was terminated early because of confirmation of benefit that had recently been shown in other trials, and the inability to extend the efficacy of bucindolol to patient subgroups that had not been previously evaluated in large scale clinical trials (BEST Investigators, 2001). At that time, there was no significant difference in mortality observed between those treated with bucindolol or with a placebo. In distinct contrast to the results of BEST, similar studies with the β-adrenergic antagonists bisoprolol (termed "CIBIS-II" trial), metoprolol (termed "MERIT-HF" trial), and carvedilol (termed "COPERNICUS" trial) reported very favorable differences (34-35% reductions in mortality) between those treated with the antagonists and those treated with a placebo. The BEST investigators speculated that one possible explanation for the difference in the results "may derive from the unique pharmacological properties of bucindolol."

In the CIBIS-II trial, the study was also stopped early, but because the mortality rates were significantly less in those treated with bisoprolol. CIBIS-II Investigators, 1999. Similarly, in the MERIT-HF study with metoprolol, the study was ended prematurely because the predefined criterion had been met and exceeded. MERIT-HF Study Group, 1999. The COPERNICUS study involving carvedilol was also halted early because of the significant benefits observed with treatment. Packer et al., 2001. The BEST investigators noted that their results raised questions about the equivalency of β-blockers.

Therefore, there are therapeutic differences between bucindolol and other β-blockers, and there was a significant question regarding the therapeutic efficacy of bucindolol overall. Consequently, any relationship between bucindolol and particular genetic variants was not evident.

The benefit of retrospective analysis based on the genetic data disclosed herein highlights the unique pharmacologic features of bucindolol that contribute to its effectiveness in treating heart failure patients. Two of these features are also instrumental in the interaction of the drug with the adrenergic receptor gene variants.

The first of these features is sympatholysis, or the ability of a drug to lower adrenergic drive directly (lower norepinephrine levels in blood and tissue). As noted above, among β-blockers that have been used to treat heart failure, bucindolol is unique in this regard (BEST Trial Investigators, 2001; Lowes et al., 2000; Bristow et al., 2004). The sympatholytic effects of bucindolol are likely due to $β_2$-receptor blockade coupled with not enough $α_1$-blockade to activate adrenergic drive. Other properties of bucindolol that could contribute to sympatholysis are nitric oxide generation and $β_3$-receptor agonism (Strosberg, 1997). These latter two properties, plus or minus weak $α_1$-receptor blockade, likely account for the mild vasodilator properties of bucindolol (Gilbert et al., 1990) which, unlike carvedilol, are not sufficiently powerful to trigger reflex adrenergic activation.

When present in modest amounts, (smaller reductions in norepinephrine) sympatholysis is a favorable property, contributing to the therapeutic anti-adrenergic effect of bucindolol. This is a potentially superior mechanism of action to simple β-blockade, as excess norepinephrine is removed from the system. Norepinephrine is toxic to heart muscle and in excess amounts triggers various cardiac disease pathways. However, when exaggerated, sympatholysis can be harmful, and can increase mortality (Bristow et al. 2004). As discussed below, genetic targeting of bucindolol allows this property to function only in a favorable manner.

Figure 13:
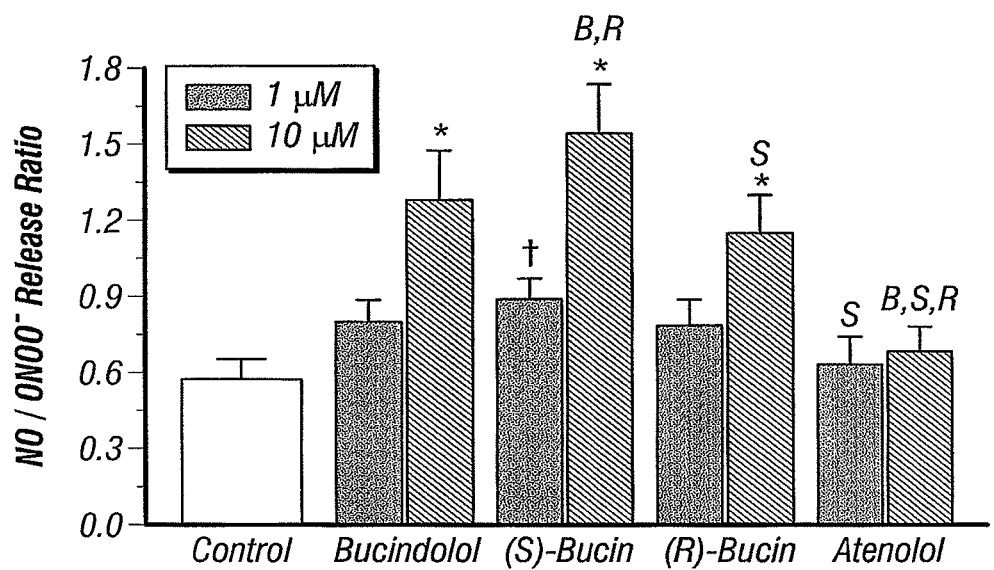
FIG. 13 Effects of bucindolol, (S)-bucindolol, (R)-bucindolol and atenolol on CaI-stimulated NO/ONOO⁻ release in HUVECs isolated from African American donors. Values are reported as mean±S.D. (N=4-5). *$p<0.001$, and †$P<0.01$ versus control; $^B p<0.01$ versus cognate bucindolol treatment; $^S p<0.05$ versus cognate (S)-bucindolol treatment; and $^R p<0.001$ versus cognate (R)-bucindolol treatment (ANOVA Student-Newman-Keuls multiple comparisons test; Overall ANOVA: $p<0.0001$; $F=30.266$). Abbreviations: (S)-Bucin=(S)-Bucindolol; (R)-Bucin=(R)-Bucindolol.

The second pharmacologic property of bucindolol that interacts with a pharmacogenetic target is high affinity $β_1$-receptor blockade (Hershberger et al., 1990; Asano et al., 2001). Bucindolol has high affinity for human $β_1$-receptors, as well as for $β_2$-receptors (Hershberger et al., 1990). In addition, through a non-agonist effect on either translation or protein turnover, bucindolol lowers $β_1$-receptor density (Asano et al., 2001). Because it is so well tolerated, bucindolol can be administered at very high β-blocking doses, and in addition bucindolol uniquely (compared to carvedilol or metoprolol) inactivates constitutively active $β_1$ 389Arg/Arg receptors (Liggett et al., 2006; Walsh et al., 2008) and each of these properties contributes to its salutary effects on the high functioning human $β_1$-receptor 389Arg/Arg gene variant (Examples, Mason et al., 1999; Liggett et al. 2006). Although bucindolol has intrinsic sympathomimetic activity (ISA) in rat myocardium in functioning human cardiac tissue bucindolol is devoid of ISA (Bristow et al., 1994; Sederberg et al., 2000; Bristow et al., 1998, Example 7). This can clearly be seen in FIG. 13, panels A and B, where no significant increase in force development occurs in isolated failing human right ventricular trabeculae, even in the presence of signal transduction augmentation with the diterpene compound forskolin, in either the $β_1$AR Arg/Arg or Gly carrier genotypes. In contrast, as shown in FIG. 13 panel C, xamoterol as a positive control ISA compound exhibits an increase in force in both low and high signal transduction activation in the $β_1$AR Arg/Arg genotype, but only in the high activation state rendered by forskolin pretreatment in Gly carriers. Finally, as shown in FIG. 13, in preparations of isolated human heart, bucindolol has unique effects on $β_1$AR Arg/Arg vs Gly carrier receptors. Under conditions of low levels of signal transduction (low receptor activation) in the failing heart (Panel A), bucindolol functions as a neutral antagonist (no agonist or inverse agonist activity) at the human myocardial $β_1$Arg/Arg receptor, but when signal transduction is high as when adenylyl cyclase is directly activated by forskolin (Panel B), bucindolol functions as an inverse agonist, inactivating the receptor as indicated by a statistically significant slope factor up to the highest concentration achievable in plasma by therapeutic doses, 10-6 M. No such effect occurs in Gly carrier receptors, where bucindolol functions as an inverse agonist in low activation states, and a neutral antagonist in the presence of forskolin. These data suggest that bucindolol is uniquely effective in antagonizing high activation states of the $β_1$389Arg/Arg receptor, the form of the receptor that would be expected to be the most cardiomyopathic.

These properties are likely reasons for the surprising and unexpected results that were observed with the Arg389 genetic variant in the $β_1$AR and the Del322-325 genetic variant in $α_{2c}$AR in the context of bucindolol treatment.

3. Stereoisomers of Bucindolol

Racemic mixtures of bucindolol or its stereoisomers can be obtained from commercial sources or can be produced by methods well-known to those of ordinary skill in the art. Commercial sources of bucindolol and its enantiomers include Knoll AG and Bristol-Myers Squib Co. Information regarding synthesis of bucindolol can be obtained from any of a variety of sources known to those of ordinary skill in the art, such as U.S. Pat. No. 6,927,036 and WO 1987003584, each of which is herein specifically incorporated by reference.

S-bucindolol can also be prepared by the resolution of racemic materials, using conventional means such as fractional crystallization, simple crystallization and chromatography on a chiral substrate, extraction, distillation, column chromatography, high performance liquid chromatography, and the like. Additional information regarding preparation of S-bucindolol and separation of S-bucindolol from a racemic mixture is discussed in the specification below.

B. PREVENTION AND THERAPY

1. Diseases to be Treated or Prevented

Some embodiments of the present invention concern methods of treating a patient. The patient may have any disease or condition for which treatment of S-bucindolol is indicated. For example, the disease or condition may be one for which treatment with a NO-enhancer is indicated. The disease or condition may be one for which treatment with a beta-blocker is indicated. Examples of such diseases and conditions are discussed elsewhere in this specification.

"Treatment" and "treating" as used herein refer to administration or application of a therapeutic agent to a subject or performance of a procedure or modality on a subject for the purpose of obtaining a therapeutic benefit of a disease or health-related condition. For example, a pharmaceutical composition that includes S-bucindolol may be administered to a subject to reduce the symptoms of congestive heart failure.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, reducing the symptoms of congestive heart failure may include reducing peripheral edema or increasing exercise tolerance.

Other embodiments of the present invention concern methods of preventing a disease in a patient. "Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition. For example, a composition comprising S-bucindolol may be administered to a patient to prevent onset of a myocardial infarction or to prevent the development of symptoms associated with congestive heart failure.

2. Routes of Administration

Administration of the pharmaceutical compositions comprising S-bucindolol set forth herein may be by any number of routes including, but not limited to oral, intravenous, intramuscular, intra-arterial, intramedullary, intrathecal, intraventricular, intradermal, intratracheal, intravesicle, intraocular, transdermal, subcutaneous, intraperitoneal, intranasal, enteral, topical, sublingual, or rectal. Further details on techniques for formulation and administration may be found in the latest edition of Remington's Pharmaceutical Sciences (Maack Publishing Co., Easton, Pa.). In certain embodiments bucindolol is formulated for oral administration.

3. Formulations

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically" or "pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free-base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4. Controlled/Extended/Sustained/Prolonged Release Administration

Another aspect of this invention provides methods of treating patients by delivering the pharmaceutical compositions set forth herein as a controlled release formulation. As used herein, the terms "controlled," "extended," "sustained," or "prolonged" release of the composition of the present invention will collectively be referred to herein as "controlled release," and includes continuous or discontinuous, and linear or non-linear release of the composition of the present invention. There are many advantages for a controlled release formulation of β-blockers.

a. Tablets

A controlled release tablet suitable for purposes of this invention is disclosed in U.S. Pat. No. 5,126,145, which is incorporated by reference herein. This tablet comprises, in admixture, about 5-30% high viscosity hydroxypropyl methyl cellulose, about 2-15% of a water-soluble pharmaceutical binder, about 2-20% of a hydrophobic component such as a waxy material, e.g., a fatty acid, and about 30-90% active ingredient.

b. Films

This invention further provides a prophylaxis for or method of treating a patient following an invasive cardiac procedure comprising administering biodegradable, biocompatible polymeric film comprising S-bucindolol, to a patient. The polymeric films are thin compared to their length and breadth. The films typically have a uniform selected thickness between about 60 micrometers and about 5 mm. Films of between about 600 micrometers and 1 mm and between about 1 mm and about 5 mm thick, as well as films between about 60 micrometers and about 1000 micrometers, and between about 60 and about 300 micrometers are useful in the manufacture of therapeutic implants for insertion into a patient's body. The films can be administered to the patient in a manner similar to methods used in adhesion surgeries. For example, a β-blocker, such as bucindolol, film formulation can be sprayed or dropped onto a cardiac tissue site or artery during surgery, or a formed film can be placed over the selected tissue site. In an alternative embodiment, the film can be used as controlled release coating on a medical device such as a stent, as is discussed in further detail below.

Either biodegradable or nonbiodegradable polymers may be used to fabricate implants in which the β-blocker is uniformly distributed throughout the polymer matrix. A number of suitable biodegradable polymers for use in making the biodegradable films of this invention are known to the art, including polyanhydrides and aliphatic polyesters, preferably polylactic acid (PLA), polyglycolic acid (PGA) and mixtures and copolymers thereof, more preferably 50:50 copolymers of PLA:PGA and most preferably 75:25 copolymers of PLA:PGA. Single enantiomers of PLA may also be used, preferably L-PLA, either alone or in combination with PGA. Polycarbonates, polyfumarates and caprolactones may also be used to make the implants of this invention.

The amount of the S-bucindolol to be incorporated into the polymeric films of this invention is an amount effective to show a measurable effect in treating diseases having similar pathophysiological states, such as but not limited to, heart failure, pheochromocytoma, migraines, cardiac arrhythmias, hypertension, aschemia, cardiomyopathy, and various anxiety disorders. The composition of the present invention can be incorporated into the film by various techniques such as by solution methods, suspension methods, or melt pressing.

c. Transdermal Patch Device

Transdermal delivery involves delivery of a therapeutic agent through the skin for distribution within the body by circulation of the blood. Transdermal delivery can be compared to continuous, controlled intravenous delivery of a drug using the skin as a port of entry instead of an intravenous needle. The therapeutic agent passes through the outer layers of the skin, diffuses into the capillaries or tiny blood vessels in the skin and then is transported into the main circulatory system.

Transdermal patch devices that provide a controlled, continuous administration of a therapeutic agent through the skin are also well known in the art. Such devices, for example, are disclosed in U.S. Pat. Nos. 4,627,429; 4,784,857; 5,662,925; 5,788,983; and 6,113,940, which are all incorporated herein by reference. Characteristically, these devices contain a drug impermeable backing layer which defines the outer surface of the device and a permeable skin attaching membrane, such as an adhesive layer, sealed to the barrier layer in such a way as to create a reservoir between them in which the therapeutic agent is placed. In one embodiment of the present invention a formulation of the β-blocker is introduced into the reservoir of a transdermal patch and used by a patient who is homozygous Arg389 at the $β_1AR$ genes.

5. Medical Devices

Another embodiment contemplates the incorporation of S-bucindolol or a composition comprising S-bucindolol as set forth herein into a medical device that is then positioned to a desired target location within the body, whereupon the S-bucindolol elutes from the medical device. As used herein, "medical device" refers to a device that is introduced temporarily or permanently into a mammal for the prophylaxis or therapy of a medical condition. These devices include any that are introduced subcutaneously, percutaneously or surgically to rest within an organ, tissue or lumen. Medical devices include, but are not limited to, stents, synthetic grafts, artificial heart valves, artificial hearts and fixtures to connect the prosthetic organ to the vascular circulation, venous valves, abdominal aortic aneurysm (AAA) grafts, inferior venal caval filters, catheters including permanent drug infusion catheters, embolic coils, embolic materials used in vascular embolization (e.g., PVA foams), mesh repair materials, a Dracon vascular particle orthopedic metallic plates, rods and screws and vascular sutures.

In one embodiment, the medical device such as a stent or graft is coated with a matrix. The matrix used to coat the stent or graft according to this invention may be prepared from a variety of materials. A primary requirement for the matrix is that it be sufficiently elastic and flexible to remain unruptured on the exposed surfaces of the stent or synthetic graft.

6. Dosages

The amount of S-bucindolol or composition comprising S-bucindolol that is administered or prescribed to the patient can be about, at least about, or at most about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg of total bucindolol or S-bucindolol, or any range derivable therein. Alternatively, the amount administered or prescribed may be about, at least about, or at most about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 mg/kg of total bucindolol or S-bucindolol, or any range derivable therein, with respect to the weight of the patient.

When provided in a discrete amount, each intake of S-bucindolol or composition comprising S-bucindolol can be considered a "dose." A medical practitioner may prescribe or administer multiple doses over a particular time course (treatment regimen) or indefinitely.

The therapeutic composition may be administered 1, 2, 3, 4, 5, 6, 7, 8, 9, 10, 11, 12, 13, 14, 15, 16, 17, 18, 19, 20, 30, 40, 50, 60, 70, 80, or more times or any range derivable therein. It is further contemplated that the drug may be taken for an indefinite period of time or for as long as the patient exhibits symptoms of the medical condition for which the therapeutic agent was prescribed. Also, the drug may be administered every 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months or more, or any range derivable therein. Alternatively, it may be administered systemically over any such period of time and be extended beyond more than a year.

C. OTHER THERAPEUTIC OPTIONS

In certain embodiments of the invention, methods may involve administering a beta-blocker that is not bucindolol for the treatment of a disease or disorder in a subject. These agents may be prescribed or administered instead of or in addition to bucindolol.

As a second therapeutic regimen, the agent may be administered or taken at the same time as S-bucindolol, or either before or after S-bucindolol. The treatment may improve one or more symptoms of disease such as providing increased exercise capacity, increased cardiac ejection volume, decreased left ventricular end diastolic pressure, decreased pulmonary capillary wedge pressure, increased cardiac output or cardiac index, lowered pulmonary artery pressures, decreased left ventricular end systolic and diastolic dimensions, decreased left and right ventricular wall stress, decreased wall tension and wall thickness, increased quality of life, and decreased disease-related morbidity and mortality.

In another embodiment, it is envisioned to use S-bucindolol in combination with other therapeutic modalities. Thus, in addition to the therapies described above, one may also provide to the patient more "standard" pharmaceutical cardiac therapies. Examples of other therapies include, without limitation, other beta blockers, anti-hypertensives, cardiotonics, anti-thrombotics, vasodilators, hormone antagonists, iontropes, diuretics, endothelin antagonists, calcium channel blockers, phosphodiesterase inhibitors, ACE inhibitors, angiotensin type 2 antagonists and cytokine blockers/inhibitors, and HDAC inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the therapy using S-bucindolol may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either S-bucindolol, or the other agent will be desired. In this regard, various combinations may be employed. By way of illustration, where the S-bucindolol is "A" and the other agent is "B", the following permutations based on 3 and 4 total administrations are exemplary:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are likewise contemplated.

1. Pharmacological Therapeutic Agents

Pharmacological therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In addition, it should be noted that any of the following may be used to develop new sets of cardiac therapy target genes as β-blockers were used in the present examples (see below). While it is expected that many of these genes may overlap, new gene targets likely can be developed.

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

Non-limiting examples of resins/bile acid sequesterants include cholestyramine (cholybar, questran), colestipol (colestid) and polidexide.

Non-limiting examples of HMG CoA reductase inhibitors include lovastatin (mevacor), pravastatin (pravochol) or simvastatin (zocor).

Non-limiting examples of nicotinic acid derivatives include nicotinate, acepimox, niceritrol, nicoclonate, nicomol and oxiniacic acid.

Non-limiting examples of thyroid hormones and analogs thereof include etoroxate, thyropropic acid and thyroxine.

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

Non-limiting examples of an antiarteriosclerotic include pyridinol carbamate.

In certain embodiments, administration of an agent that aids in the removal or prevention of blood clots may be combined with administration of a modulator, particularly in treatment of athersclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

Non-limiting examples of antiplatelet agents include aspirin, a dextran, dipyridamole (persantin), heparin, sulfinpyranone (anturane) and ticlopidine (ticlid).

Non-limiting examples of thrombolytic agents include tissue plaminogen activator (activase), plasmin, pro-urokinase, urokinase (abbokinase) streptokinase (streptase), anistreplase/APSAC (eminase).

In certain embodiments wherein a patient is suffering from a hemmorage or an increased likelyhood of hemmoraging, an agent that may enhance blood coagulation may be used. Non-limiting examples of a blood coagulation promoting agent include thrombolytic agent antagonists and anticoagulant antagonists.

Non-limiting examples of anticoagulant antagonists include protamine and vitamine K1.

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrythmic agents (calcium channel blockers) and miscellaneous antiarrythmic agents.

Non-limiting examples of sodium channel blockers include Class IA, Class IB and Class IC antiarrythmic agents. Non-limiting examples of Class IA antiarrythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor).

Non-limiting examples of a beta blocker, otherwise known as a β-adrenergic blocker, a β-adrenergic antagonist or a Class II antiarrhymic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

Non-limiting examples of an agent that prolong repolarization, also known as a Class III antiarrhythmic agent, include amiodarone (cordarone) and sotalol (betapace).

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

Non-limiting examples of miscellaneous antiarrhymic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

In certain embodiments, an antihypertensive agent is both an alpha and beta adrenergic antagonist. Non-limiting examples of an alpha/beta blocker comprise labetalol (normodyne, trandate).

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Non-limiting examples of arylethanolamine derivatives include amosulalol, bufuralol, dilevalol, labetalol, pronethalol, sotalol and sulfinalol.

Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Non-limiting examples of dihydropyridine derivatives include amlodipine, felodipine, isradipine, nicardipine, nifedipine, nilvadipine, nisoldipine and nitrendipine.

Non-limiting examples of guanidine derivatives include bethanidine, debrisoquin, guanabenz, guanacline, guanadrel, guanazodine, guanethidine, guanfacine, guanochlor, guanoxabenz and guanoxan.

Non-limiting examples of hydrazines/phthalazines include budralazine, cadralazine, dihydralazine, endralazine, hydracarbazine, hydralazine, pheniprazine, pildralazine and todralazine.

Non-limiting examples of imidazole derivatives include clonidine, lofexidine, phentolamine, tiamenidine and tolonidine.

Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Non-limiting examples of reserpine derivatives include bietaserpine, deserpidine, rescinnamine, reserpine and syrosingopine.

Non-limiting examples of sulfonamide derivatives include ambuside, clopamide, furosemide, indapamide, quinethazone, tripamide and xipamide.

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

Non-limiting examples of agents for the treatment of congestive heart failure include anti-angiotension II agents, afterload-preload reduction treatment, diuretics and inotropic agents.

In certain embodiments, an animal patient that cannot tolerate an angiotension antagonist may be treated with a combination therapy. Such therapy may combine administration of hydralazine (apresoline) and isosorbide dinitrate (isordil, sorbitrate).

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

2. Surgical Therapeutic Agents

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

D. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effects of Bucindolol and its Enantiomers on Nitric Oxide and Peroxynitrite Release from White, African American and Mexican American Endothelial Cells: Comparison to Atenolol Methods Donors and Cell Cultures.

Human umbilical vein endothelial cells were isolated into primary cultures from healthy female donors by Clonetics (San Diego, Calif.) and purchased as proliferating cells. All cell culture donors were healthy, with no pregnancy or pre-natal complications. None of the donors took any drugs regularly and all were nonsmokers and consumed regular caloric/content diet. The cultured cells were incubated in 95% air/5% $CO_2$ at 37° C. and passage by an enzymatic (trypsin) procedure. The confluent cells (4 to $5\times10^5$ cells per 35-mm dish) were placed with minimum essential medium containing 3 mM L-arginine and 0.1 mM (6R)-5,6,7,8-tetrahydrobiopterin ($BH_4$). Before the experiments, the cells (from second or third passage) were rinsed twice with Tyrode-HEPES buffer with 1.8 mM CaCl2. Bucindolol and its enanatiomers were obtained from Arca Discovery (Denver, Colo.).

Measurement of NO and $ONOO^-$ Levels.

Measurement of NO was carried out with electrochemical nanosensors (FIG. 1). Their design was based on previously developed and well-characterized chemically modified carbon-fiber technology (Lvovich and Scheeline, 1997; Malinski and Taha, 1992). Each of the nanosensors was constructed by depositing a sensing material on the tip of a carbon fiber (length 4-5 µm, diameter 0.2-0.5 µm). The fibers were sealed with nonconductive epoxy and electrically connected to copper wires with conductive silver epoxy. The inventors used a conductive film of polymeric nickel (II) tetrakis(3-methoxy-4-hydroxyphenyl) porphyrin for the NO-sensor.

The NO nanosensors (diameter 1-2 µm) with a platinum wire (0.1 mm) counter electrode and saturated calomel reference electrode (SCE) were applied. Differential pulse voltammetry (DPV) and amperometry were performed with a computer-based Gamry VFP600 multichannel potentiostat. DPV was used to measure the basal NO concentrations, and amperometry was used to measure changes in NO concentrations from its basal level with time. The DPV current at the peak potential characteristic for NO oxidation (0.65 V) reduction was directly proportional to the local concentrations of these compounds in the immediate vicinity of the sensor. Linear calibration curves (current vs. concentration) were constructed for each sensor from 10 nM to 3 µM before and after measurements with aliquots of NO standard solutions, respectively. The detection limit of the sensors was 1.0 nM.

The quantification of each analyte (concentration in nmol/L) was performed using a maximum current from amperograms and standard calibration curves. The reproducibility of measurements with nanosensors is relatively high, as previously described (Lvovich and Scheeline, 1997; Malinski and Taha, 1992). The NO nanosensor modules were lowered with the help of a computer-controlled micromanipulator until it reached the surface of the cell membrane (a small piezoelectric signal, 0.1-0.2 pA, of 1-3 milliseconds duration was observed at this point). The sensors were slowly raised 5±2 µm from the surface of a single endothelial cell.

The HUVEC preparation is stable over the course of these experiments with the cells remaining viable and active responses to NO stimulation in culture for >24 hours. For robust statistical analysis, randomly selected cells were used for each concentration and type of drug used in these analyses.

Results

Figure 2:
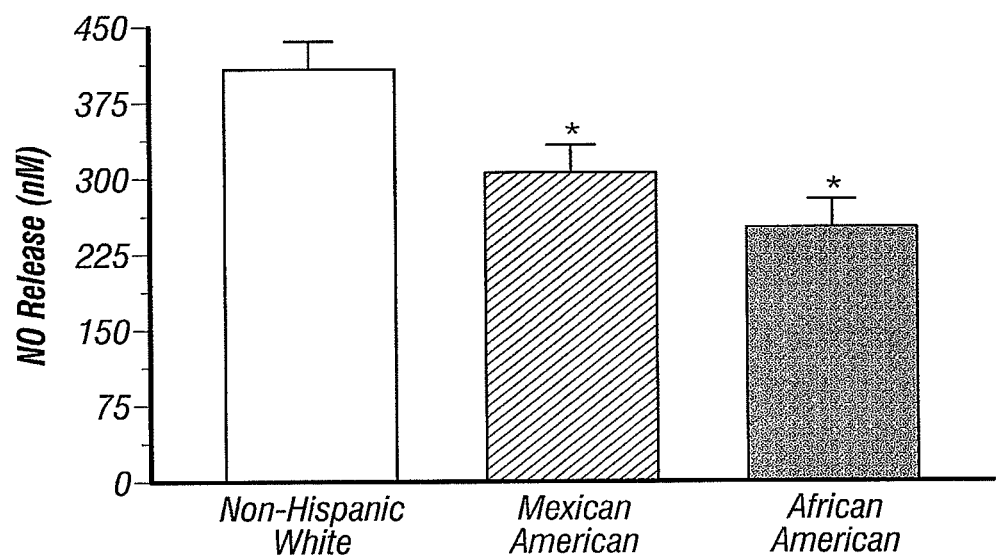
FIG. 2. CaI-stimulated NO release in HUVECs isolated from non-Hispanic white, Mexican American and African American donors. Values are reported as mean±S.D. (N=5). *$p<0.01$ versus Non-Hispanic white controls (ANOVA Dunnett multiple comparisons test; Overall ANOVA: $p<0.0001$; F=47.375).

This study demonstrated reduced NO bioavailability in tissue from patients in high-risk populations for hypertension, such as African Americans and Mexican Americans. As shown in FIG. 2, endothelial-dependent NO release from Mexican American and African American donors was 25% (305±28 nM, mean±S.D.) and 39% (251±27 nM) lower, respectively, than in non-Hispanic whites (409±23 nM), following stimulation with a receptor-independent stimulus (1.0 µM CaI).

Figure 3:
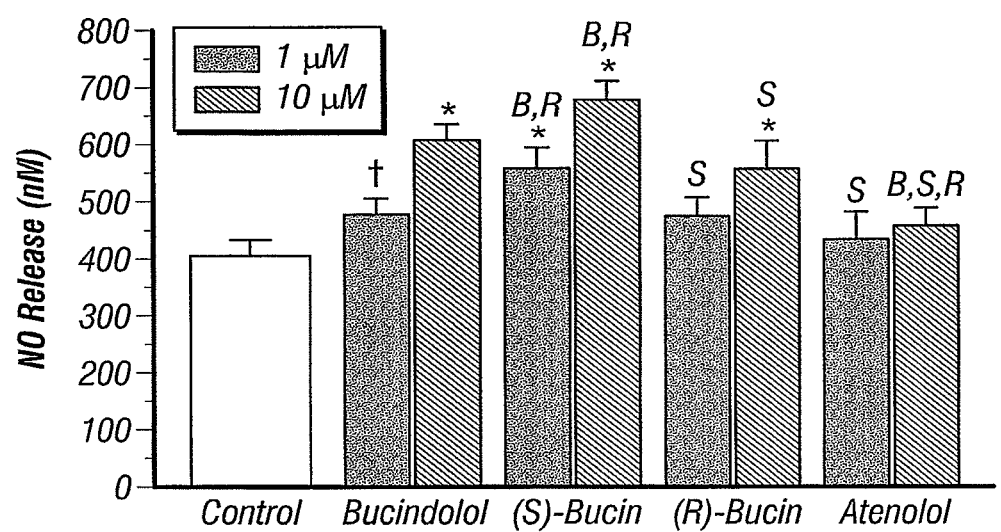
FIG. 3. Effects of bucindolol, (S)-bucindolol, (R)-bucindolol and atenolol on CaI-stimulated NO release in HUVECs isolated from non-Hispanic white donors. Values are reported as mean±S.D. (N=4-5). *$p<0.001$ and †$p<0.05$ versus control; $^B p<0.01$ versus cognate bucindolol treatment; $^S p<0.001$ versus cognate (S)-bucindolol treatment; and $^R p<0.001$ versus cognate (R)-bucindolol treatment (ANOVA Student-Newman-Keuls multiple comparisons test; Overall ANOVA: $p<0.0001$; F=31.062). Abbreviations: (S)-Bucin=(S)-Bucindolol; (R)-Bucin=(R)-Bucindolol.
Figure 4:
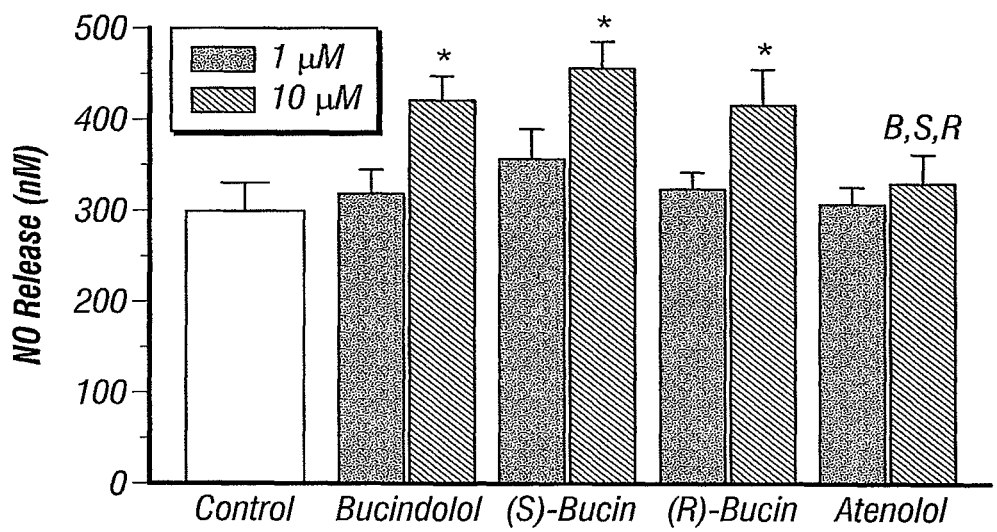
FIG. 4 Effects of bucindolol, (S)-bucindolol, (R)-bucindolol and atenolol on CaI-stimulated NO release in HUVECs isolated from Mexican-American donors. Values are reported as mean±S.D. (N=4-5). *$p<0.001$ versus control; $^B p<0.001$ versus cognate bucindolol treatment; $^S p<0.001$ versus cognate (S)-bucindolol treatment; and $^R p<0.001$ versus cognate (R)-bucindolol treatment (ANOVA Student-Newman-Keuls multiple comparisons test; Overall ANOVA: $p<0.0001$; F=19.458). Abbreviations: (S)-Bucin=(S)-Bucindolol; (R)-Bucin=(R)-Bucindolol.
Figure 5:
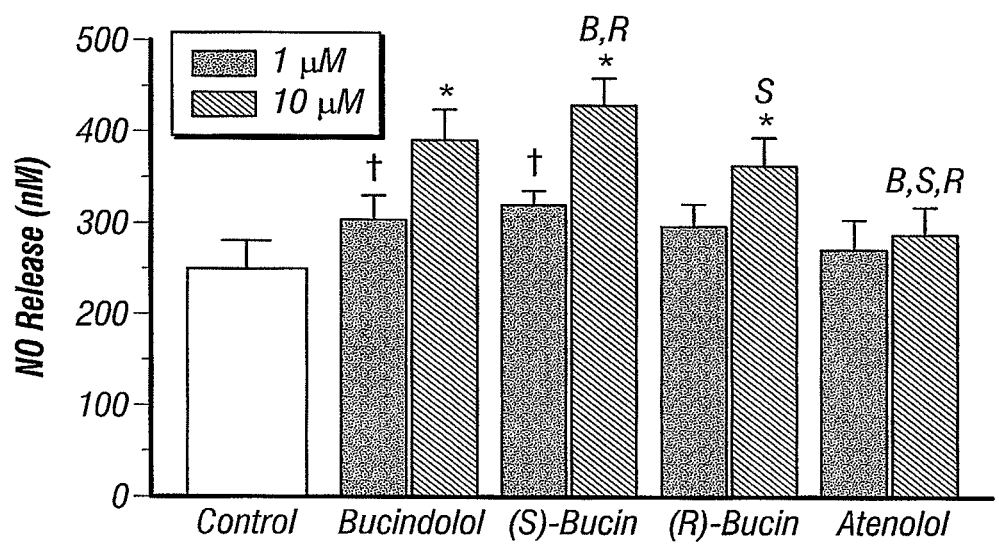
FIG. 5 Effects of bucindolol, (S)-bucindolol, (R)-bucindolol and atenolol on CaI-stimulated NO release in HUVECs isolated from African American donors. Values are reported as mean±S.D. (N=4-5). *$p<0.001$ and †$p<0.05$ versus control; $^B p<0.05$ versus cognate bucindolol treatment; $^S p<0.001$ versus cognate (S)-bucindolol treatment; and $^R p<0.01$ versus cognate (R)-bucindolol treatment (ANOVA Student-Newman-Keuls multiple comparisons test; Overall ANOVA: $p<0.0001$; F=21.419. Abbreviations: (S)-Bucin=(S)-Bucindolol; (R)-Bucin=(R)-Bucindolol.

Treatment with the $\beta_1$-selective antagonist bucindolol, and especially its active enantiomer (S)-bucindolol, caused a dose-dependent increase in the capacity of the endothelium to generate NO (FIGS. 3-5). Pretreatment (6 hr) of the cells with bucindolol racemate (1.0 µM) increased NO release and enhanced endothelial activity in white donors (16% to 475±27 nM), Mexican American donors (5% to 321±28 nM), and African American donors (22% to 306±25 nM).

Figure 6:
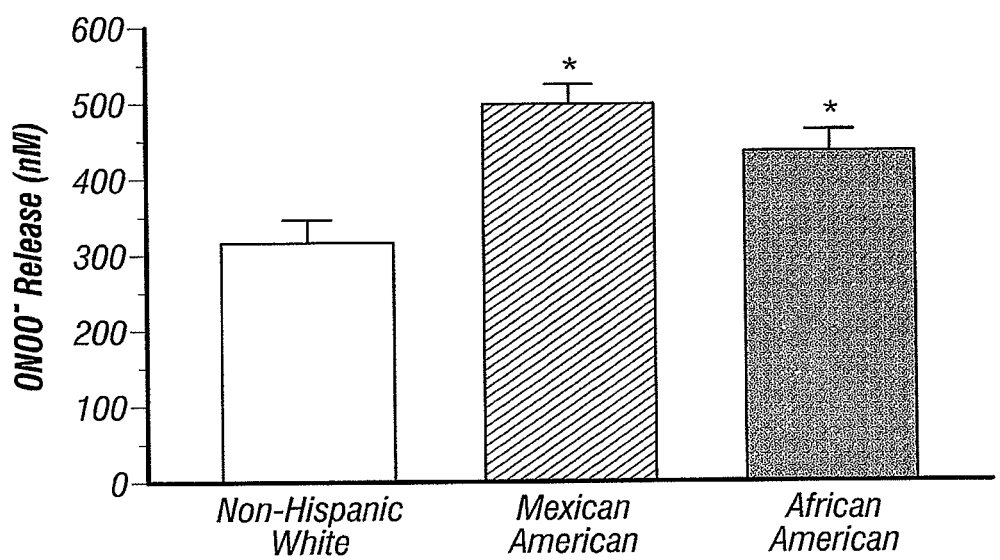
FIG. 6 CO-stimulated $ONOO^-$ release in HUVECs isolated from non-Hispanic white, Mexican American and African American donors. Values are reported as mean±S.D. (N=5). *$p<0.01$ versus control (ANOVA Dunnett multiple comparisons test; Overall ANOVA: $p<0.0001$; F=55.340).
Figure 7:
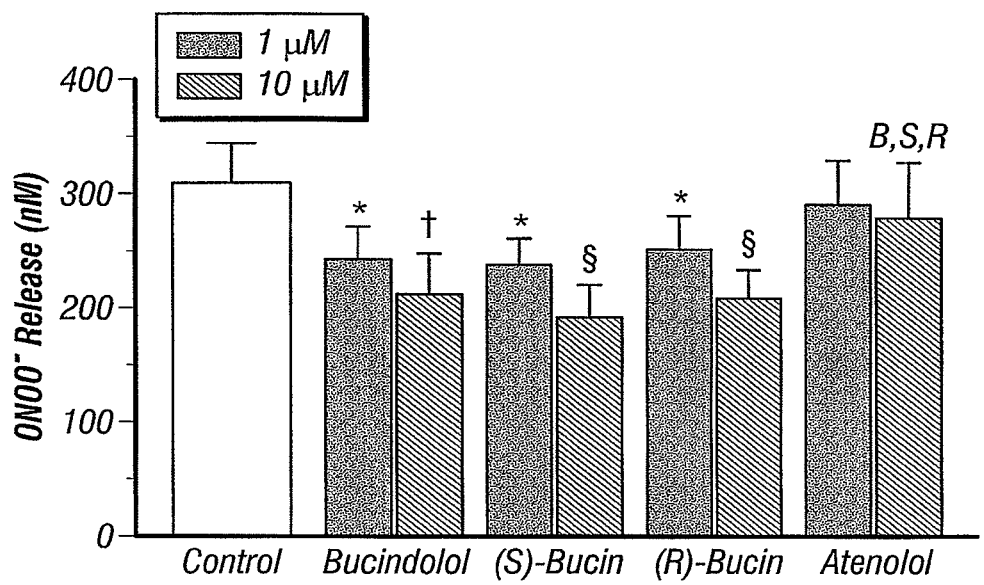
FIG. 7 Effects of bucindolol, (S)-bucindolol, (R)-bucindolol and atenolol on CaI-stimulated ONOO⁻ release in HUVECs isolated from non-Hispanic white donors. Values are reported as mean±S.D. (N=4-5). *$p<0.05$, †$p<0.01$ and §$p<0.001$ versus control; $^B p<0.05$ versus cognate bucindolol treatment; $^S p<0.01$ versus cognate (S)-bucindolol treatment; and $^R p<0.05$ versus cognate (R)-bucindolol treatment (ANOVA Student-Newman-Keuls multiple comparisons test; Overall ANOVA: $p<0.0001$; $F=7.575$). Abbreviations: (S)-Bucin=(S)-Bucindolol; (R)-Bucin=(R)-Bucindolol.
Figure 8:
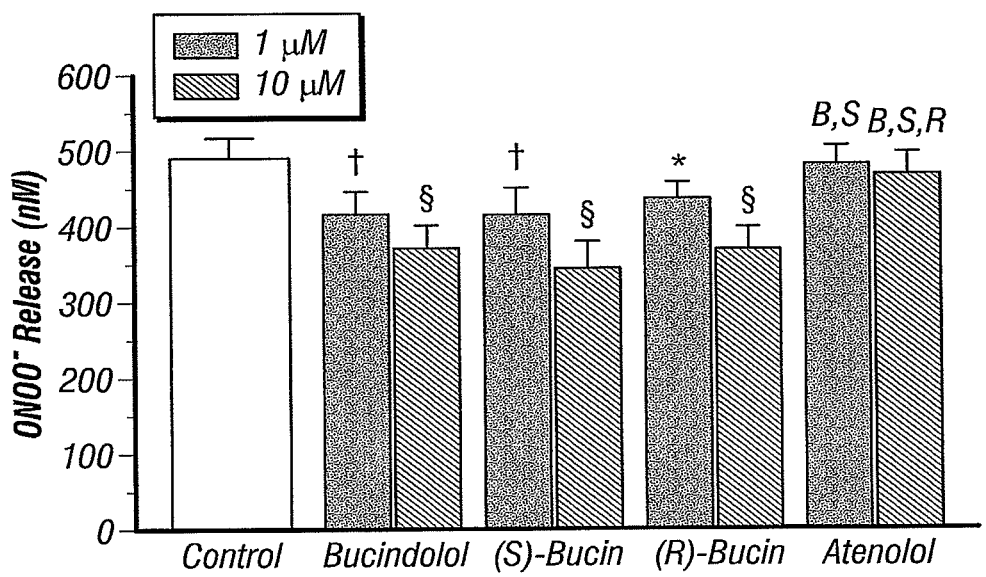
FIG. 8 Effects of bucindolol, (S)-bucindolol, (R)-bucindolol and atenolol on CaI-stimulated ONOO⁻ release in HUVECs isolated from Mexican American donors. Values are reported as mean±S.D. (N=4-5). *$p<0.05$, †$p<0.01$ and §$p<0.001$ versus control; $^B p<0.05$ versus cognate bucindolol treatment; $^S p<0.05$ versus cognate (S)-bucindolol treatment; and $^R p<0.05$ versus cognate (R)-bucindolol treatment (ANOVA Student-Newman-Keuls multiple comparisons test; Overall ANOVA: $p<0.0001$; $F=15.481$). Abbreviations: (S)-Bucin=(S)-Bucindolol; (R)-Bucin=(R)-Bucindolol.
Figure 9:
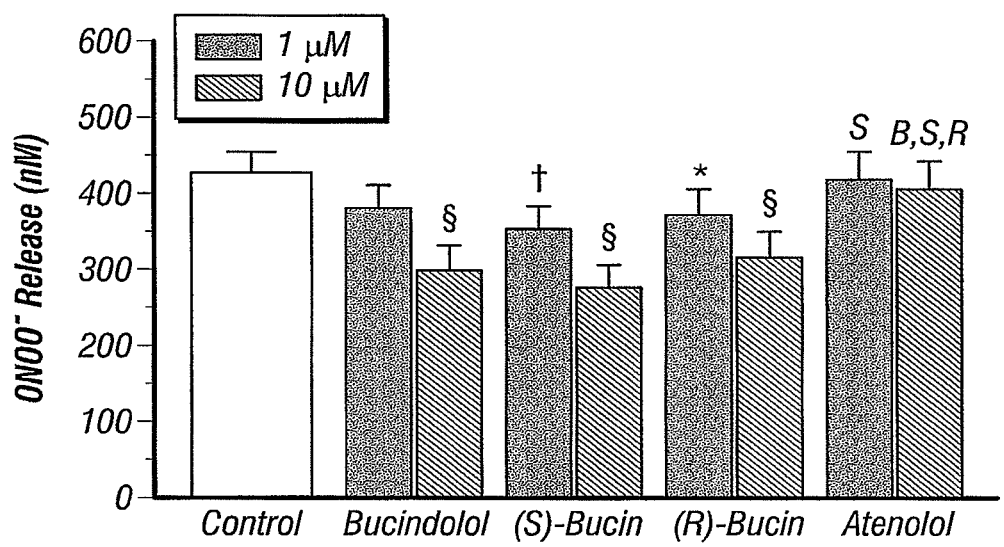
FIG. 9 Effects of bucindolol, (S)-bucindolol, (R)-bucindolol and atenolol on CaI-stimulated ONOO⁻ release in HUVECs isolated from African American donors. Values are reported as mean±S.D. (N=4-5). *$p<0.05$, †$p<0.01$ and §$p<0.001$ versus control; $^B p<0.001$ versus cognate bucindolol treatment; $^S p<0.05$ versus cognate (S)-bucindolol treatment; and $^R p<0.01$ versus cognate (R)-bucindolol treatment (ANOVA Student-Newman-Keuls multiple comparisons test; Overall ANOVA: $p<0.0001$; $F=14.628$). Abbreviations: (S)-Bucin=(S)-Bucindolol; (R)-Bucin=(R)-Bucindolol.

In addition to reduced NO production, cells from these racial groups showed evidence of increased nitroxidative stress. The release of $ONOO^-$ from Mexican American and African American donors was higher by 57% (493±26 nM) and 37% (428±26 nM), respectively, than in non-Hispanic white donors (313±30 nM), following stimulation with CaI (FIG. 6). Treatment with the bucindolol (1.0 M), and especially its active enantiomer (S)-bucindolol, caused a pronounced reduction in nitroxidative stress. Bucindolol reduced $ONOO^-$ levels by 19% (313±30 nM to 244±29 nM) in cells from non-Hispanic white donors, by 14% (493±26 nM to 422±27 nM) in cells from Mexican Americans and by 12% in cell from African Americans (428±26 nM to 378±30 nM) as shown in FIGS. 7-9. The favorable effects of bucindolol were much more apparent at 10.0 µM.

As compared to bucindolol racemate, a favorable effect on endothelial function was more pronounced with the active 1-selective enantiomer, (S)-bucindolol, while less activity was seen with (R)-bucindolol. The differences in these enanatiomers were especially evident in cells from non-Hispanic white donors. Pretreatment (6 hr) of the cells with (S)-bucindolol (1.0 µM) increased NO release and enhanced endothelial activity in white donors (35% to 553±35 nM), Mexican American donors (17% to 358±32 nM), and African American donors (27% to 318±16 nM). The (S)-bucindolol also reduced $ONOO^-$ levels by 23% to 240±24 nM in cells from non-Hispanic white donors as well as 15% to 419±34 nM in cells from Mexican Americans and 18% in cell from African Americans to 352±26 nM (FIGS. 7-9).

Figure 10:
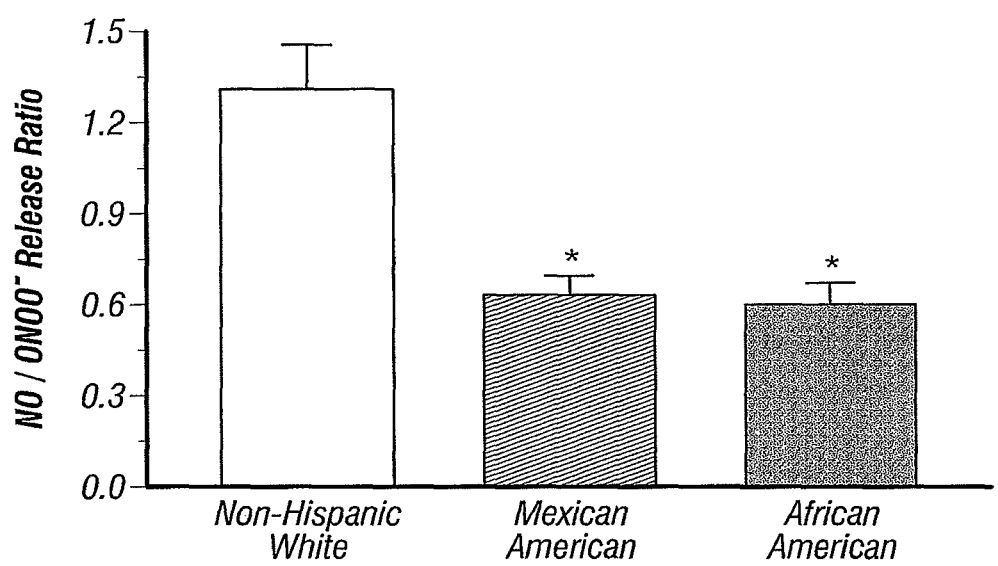
FIG. 10 CaI-stimulated NO/ONOO⁻ release ratio in HUVECs isolated from non-Hispanic white, Mexican American, and African American donors. Values are reported as mean±S.D. (N=5). *$p<0.01$ versus control (ANOVA Dunnett multiple comparisons test; Overall ANOVA: $p<0.0001$; $F=79.897$).
Figure 11:
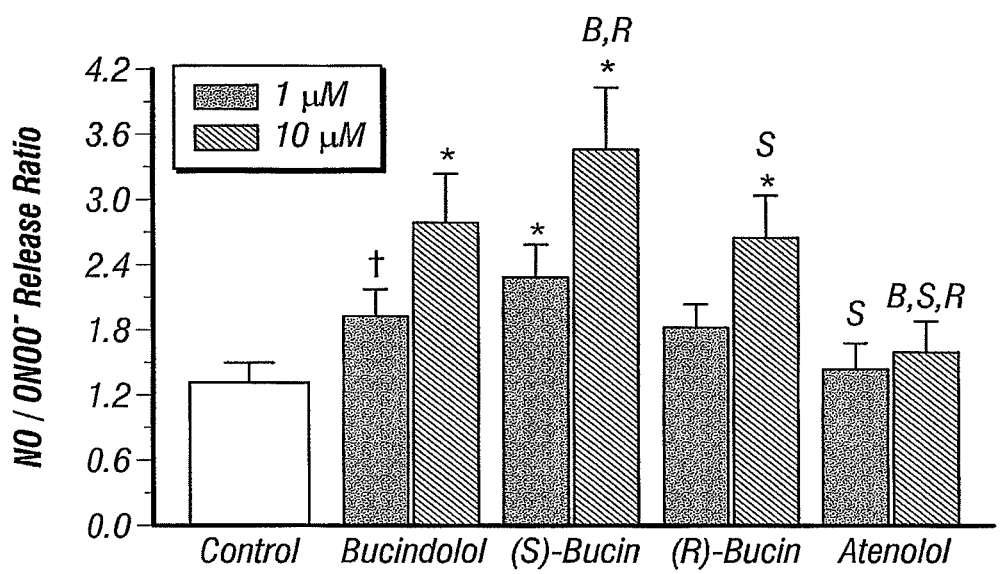
FIG. 11 Effects of bucindolol, (S)-bucindolol, (R)-bucindolol and atenolol on CaI-stimulated NO/ONOO⁻ release in HUVECs isolated from non-Hispanic white donors. Values are reported as mean±S.D. (N=4-5). *$p<0.001$, and †$p<0.05$ versus control; $^B p<0.01$ versus cognate bucindolol treatment; $^S p<0.01$ versus cognate (S)-bucindolol treatment; and $^R p<0.01$ versus cognate (R)-bucindolol treatment (ANOVA Student-Newman-Keuls multiple comparisons test; Overall ANOVA: $p<0.0001$; $F=21.782$). Abbreviations: (S)-Bucin=(S)-Bucindolol; (R)-Bucin=(R)-Bucindolol.
Figure 12:
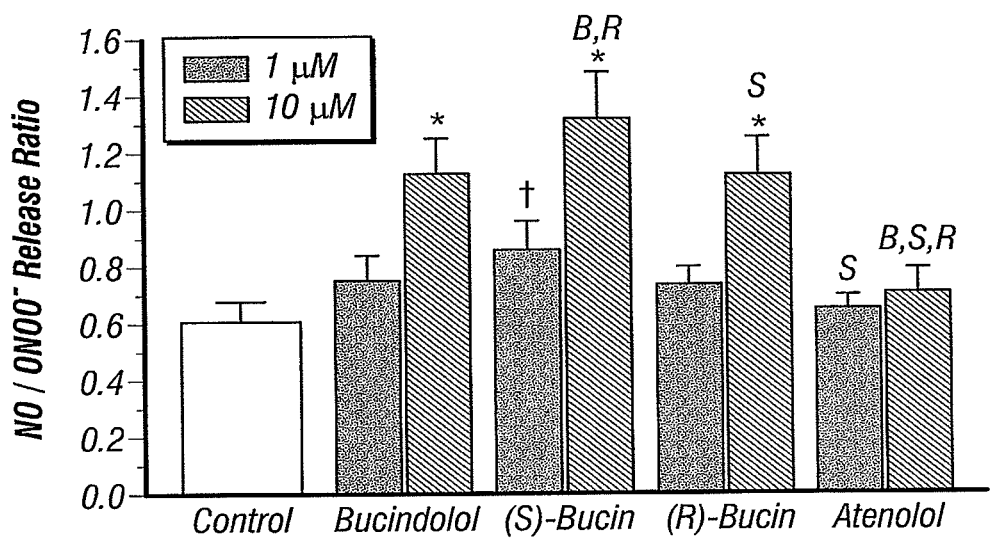
FIG. 12 Effects of bucindolol, (S)-bucindolol, (R)-bucindolol and atenolol on CaI-stimulated NO/ONOO⁻ release in HUVECs isolated from Mexican American donors. Values are reported as mean±S.D. (N=4-5). *$p<0.001$, and †$p<0.01$ versus control; $^B p<0.05$ versus cognate bucindolol treatment; $^S p<0.05$ versus cognate (S)-bucindolol treatment; and $^R p<0.05$ versus cognate (R)-bucindolol treatment (ANOVA Student-Newman-Keuls multiple comparisons test; Overall ANOVA: $p<0.0001$; $F=29.540$). Abbreviations: (S)-Bucin=(S)-Bucindolol; (R)-Bucin=(R)-Bucindolol.

The most comprehensive measurement of endothelial function is the ratio of NO to $ONOO^-$ following treatment with these agents. This study demonstrated large differences in endothelial function in tissue from higher risk populations for hypertension, such as African Americans and Mexican Americans (FIG. 10). The basis for these differences is not understood but may be due to genetic variability in the eNOS protein. Bucindolol racemate (1.0 µM) increased the NO/$ONOO^-$ ratio in white donors (49%), Mexican American donors (23%), and African American donors (38%) as shown in FIGS. 11-13. An even greater effect was observed with (S)-bucindolol. Again, the favorable effects of bucindolol and its enantiomers were much more apparent at the higher dose (10.0 µM) by at least two fold. The effect at the high concentration was especially evident in higher risks populations (African Americans, Mexican Americans). In contrast, atenolol failed to produce an effect even at the higher dose.

In summary, bucindolol had a dual effect on endothelial function by increasing the capacity of cells to generate NO while simultaneously reducing $ONOO^-$ production. The effect of bucindolol on endothelial function was dose-dependent and stereoselective; greater NO bioavailability was associated with its active enantiomer, (S)-bucindolol. The basis for the benefit with bucindolol may be due to interactions with novel receptor sites, such as the beta3 adrenergic receptor, along its property of inhibition of oxidative stress mechanisms (e.g., NADPH oxidase). The favorable activity of bucindolol on endothelial function was observed in three different racial groups, including African Americans, Mexican Americans and non-Hispanic whites. The activity of (S)-bucindolol was superior to bucindolol racemate and the 1-selective blocker atenolol.

Example 2

Stereospecificity of Bucindolol Binding to Human $\beta_1$-Adrenergic Receptors

Figure 14A:
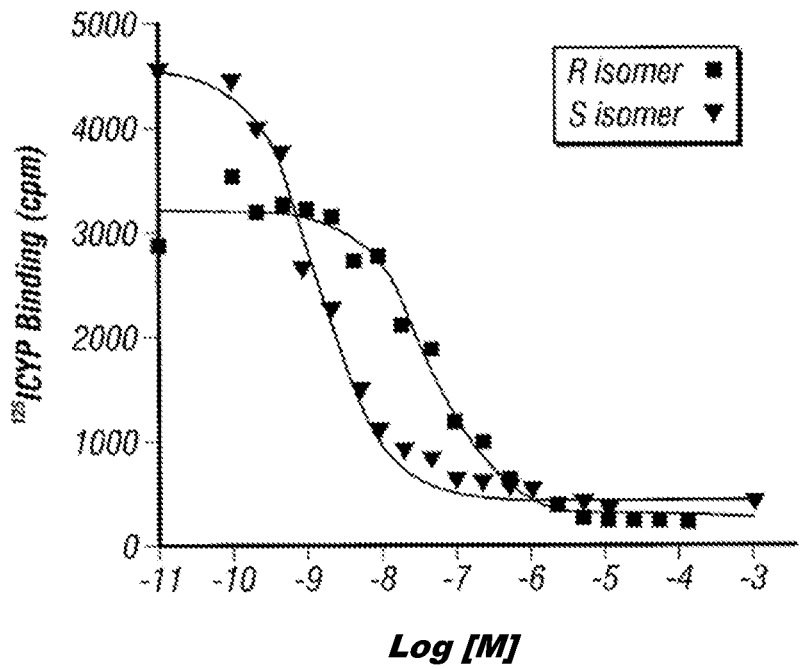
FIGS. 14A, 14B. 14A—Competition curve between S- or R-bucindolol in human LV membranes that are 86% $\beta_1$. AR and genotypically 389 Arg/Arg. The respective $K_i$s are 0.49 nM and 14.0 nM for the S- and R-isomers. 14B—Competition curve between S- or R-bucindolol in human LV membranes that are 83% $\beta_1$. AR and genotypically 389 Gly/Gly. The respective $K_i$s are 0.59 nM and 26.3 nM for the S- and R-isomers.
Figure 14B:
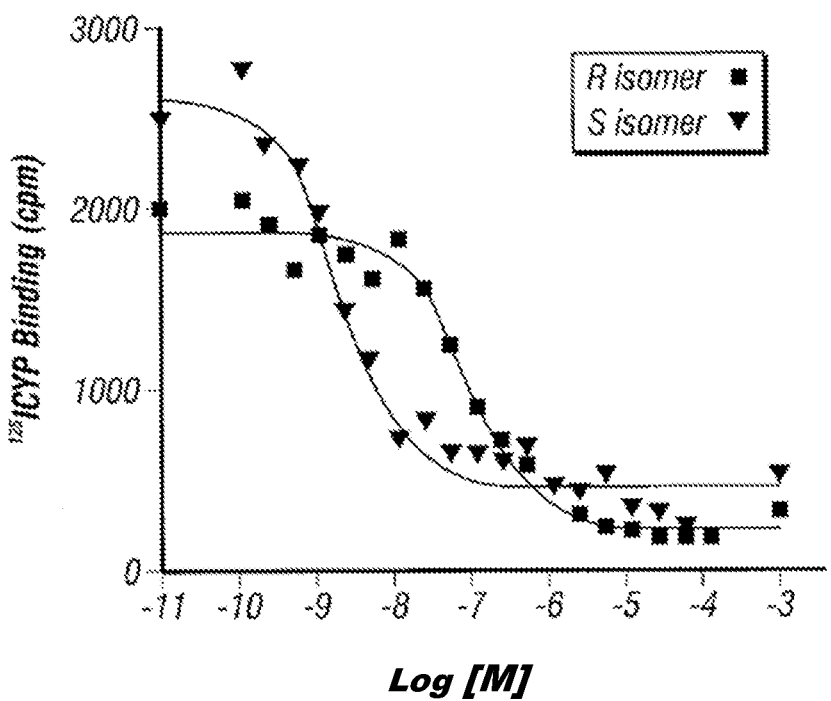

FIG. 14 gives the binding of S- and R-bucindolol in left ventricular membranes prepared from one patient who had the $\beta_1$ 389 Arg/Arg receptor (FIG. 14A), and another with the Gly/Gly (FIG. 14B) genotype. As can be observed, the S-isomer has much higher affinity, in both genotypes. In addition, the $K_i$s are similar for both the S- (0.5-0.6 nM) and R- (around 14-26 nM) isomers in the Arg/Arg and Gly/Gly preparations. Similar results were obtained in the presence of Gpp(NH)p.

Example 3

Separation of the R- and S-Enantiomers of Bucindolol Hydrochloride

Chemistry.

The usual procedure for the resolution of racemic amine derivatives involves fractional recrystallization of a mixture of the diastereomeric salts formed by combination of the base with an optically active acid (e.g. d-tartaric). With bucindolol, however, this process proved too tedious and time consuming to be practical for medium scale work (5-25 g), and an alternate method was sought.

Racemic alcohols have been resolved by separation of the corresponding diastereomeric carbamates produced by reaction with optically active arylalkyl isocyanates (Pirkle and Hoekstra, 1974; Pirkle and Hauske, 1977a; Pirkle and Hauske, 1977b). Bucindolol, with a secondary hydroxyl group in the side chain, would seem ideally suited for reaction with this type of reagent. The reaction of bucindolol with (R)-(−)-(1-naphthyl)ethyl isocyanate, however, does not provide the anticipated carbamates but gives a pair of diastereomeric urea (Kolomiets et al., 1980) derivatives incorporating the basic nitrogen (Scheme 1). The greater reactivity of the basic nitrogen is not overcome by steric hindrance from the bulky N-substituent. Resolution is achieved via these ureas.

As the benzene solubility of one of the two isomeric ureas is significantly less than the other, the initial separation becomes relatively trivial and the less soluble isomer is obtained in excellent purity. The residual material affords, by gravity column chromatography, the companion isomer in very satisfactory yield.

Generation of the individual optical antipodes is accomplished easily by stirring each diastereomer with hydrazine hydrate in ethanol solution. Treatment with pyruvic acid in this last step effectively removes the N-[(1-naphthyl)ethyl] hydrazinecarboxamide by-product and excess hydrazine.

Thus the resolution of bucindolol into its respective enantiomers is achieved via a facile new method that should be of general use for new β-blocker molecules in the future.

Assignment of absolute configuration to the enantiomers of bucindolol (MJ 13105) is tentative, and based on the usual assignment of S-configuration to the β-adrenergic aryloxypropanolamine enantiomer with negative rotation (Danilewicz and Kemp, 1973).

Experimental.

Melting points were determined using a Thomas-Hoover capillary melting point apparatus and are uncorrected. Analytical values of carbon, hydrogen, and nitrogen are within 0.4% of theory and NMR, IR, and MS spectra are consistent with the assigned structures. Optical rotation measurements were obtained on a Bendix-NPL 1169 automatic polarimeter with digital readout.

Silica gel 60 (EM Reagents) was used for column chromatography.

The (g)-(−)-(1-naphthyl)ethyl isocyanate was purchased from Aldrich Chemical Co.

2-[2-Hydroxy-3-[[2-(1H-indol-3-yl)-1,1-dimethylethyl] amino]propoxy~benzo-nitrile (MJ 13105 free base). A hot solution of bucindolol hydrochloride salt (100 g, 0.28 mol) and 2.5 l of $H_2O$ was basified with a 10% solution of NaOH. After cooling, the aqueous layer was decanted, and the residual gum rinsed with $H_2O$ and crystallized from i-PrOH (500 mL) to provide 81 g of MJ 13105 free base: mp 126-128° C.

The aqueous layer was allowed to stand overnight at 25° C., and the precipitate was collected by filtration, washed with $H_2O$, and air dried overnight to give a 3.5 g second crop of MJ 13105 free base: mp 125-127° C.

(S), (R) and (R), (R)—N-[3-(2-Cyanophenoxy)-2-hydroxypropyl]-N-1,1-dimethyl-2-(1H-indol-3-yl)ethyl]-N'-[1-(1-naphthyl)ethyl]urea. A mixture of (R,S)-bucindolol (MJ 13105) free base (1.8 g, 0.0051 mol), (R)-(−)-1-(1-naphthyl)-ethyl isocyanate (1.0 g, 0.0051 mol), and benzene (100 mL) was stirred at 25° C. for 6 h. The white solid was removed by filtration and air dried to give 1.24 g of (S), (R)—N-[3-(2-cyanophenoxy)-2-hydroxypropyl]-N-[1,1-dimethyl-2-(1H-indol-3-yl)ethyl]-N'-[1-(1-naphthyl)ethyl]urea: mp 167-168° C., one spot on TLC (silica gel; $CH_2Cl_2$/EtOAc, 9:1), $$[\alpha]\frac{25}{D} - 14° \text{ (C 0.5\%, CH}_3\text{OH)}.$$

Anal. Calcd. for $C_{35}H_{36}N_4O_3$: C, 74.98; H, 6.48; N, 10.00. Found: C, 74.89; H, 6.46; N, 9.74.

The filtrate was concentrated to dryness and the residue chromatographed on silica gel with $CH_2Cl_2$/EtOAc (9:1) to give 0.70 g of (R),(R)—N_-[3-(2-cyanophenoxy)-2-hydroxypropyl]-N-[1,1-dimethyl-2-(1H-indol-3-yl)ethyl]-N'41-(1-naphthyl)ethyl urea as a foam:

$$[\alpha]\frac{25}{D} - 119° \text{ (C 0.5\%, CH}_3\text{OH)}.$$

Anal. Calcd for $C_{35}H_{36}N_4O_3 \cdot \frac{1}{2}$ EtOAc: C, 73.49; H, 6.67; N, 9.27. Found: C, 73.29; H, 6.60; N, 9.18.

(S)-(−) and (R)-(+)-2-[2-Hydroxy-3-[[2-(1H-indol-3-yl)-1,1-dimethylethyl]-amino]propoxy]benzonitrile cyclamate (MJ 13105-163-997 and MJ 13105-163-998). The respective diastereomer of the urea derivative was heated at reflux for 0.5 h in absolute EtOH with five equivalents of 99% hydrazine hydrate. After evaporation of the solvent at reduced pressure, the residue was dissolved in $CH_3CN$, and five equivalents of pyruvic acid were added. The solution was stirred at 25° C. overnight and concentrated at. reduced pressure to give a residue that was dissolved in EtOAc. The EtOAc solution was washed with three portions each of 1 N NaOH and $H_2O$, dried (anhyd. $MgSO_4$), filtered, and concentrated. One equivalent of cyclohexanesulfamic acid was added to a solution of the weighed residue and absolute EtOH. After the mixture had cooled, the precipitated salt was collected by filtration. Recrystallization from EtOH-(i-Pr)$_2$O-(Darco G-60) gave the analytically pure samples of each isomer.

$(s)-(-)$-isomer, mp 180-181° C., $[\alpha]\frac{25}{D} - 15.0°$ (C 1, $CH_3OH$).

Anal. Calcd for $C_{22}H_{25}N_3O_2$ $C_6H_{13}NO_3S$: C, 61.98; H, 7.06; N, 10.33. Found: C, 62.12; H, 7.08; N, 10.31.

$(R)-(+)$-isomer, $-$mp 179-180° C., $[\alpha]\frac{25}{D} + 15.5°$ (C 1, $CH_3OH$).

Anal. Calcd for $C_{22}H_{25}N_3O_2$ $C_6H_{13}NO_3S$: C, 61.98; H, 7.06; N, 10.33. Found: C, 62-0.07; H, 7.14; N, 10.11.

Example 4

Determination of Percent (R)- and (S)-Bucindolol Present in Bucindolol Drug Substance and Drug Products by HPLC Summary Chiral separation of (R)- and (S)-bucindolol is achieved by HPLC for the purpose of determining the percent ratios present in drug substance or drug products (tablets or capsules).

Equipment (as Stated Below, or Equivalent)

HPLC system (equipped with a UV detector capable of detection at 220 nm)

(Accompanying data systems are acceptable for quantitation)

Chiral Technologies, Inc. Chiralpak AD (4.6 mm×25 cm) column 0.2 µm filter, Acrodisc CR PTFE 0.2 µm Product No. 4225 25 mm Reagents Reagent Alcohol (Ethanol), HPLC grade Diethylamine, reagent grade Reference Standards (R)-Bucindolol HCl Reference Standard and (S)-Bucindolol HCl Reference Standard or racemic Bucindolol HCl Reference Standard

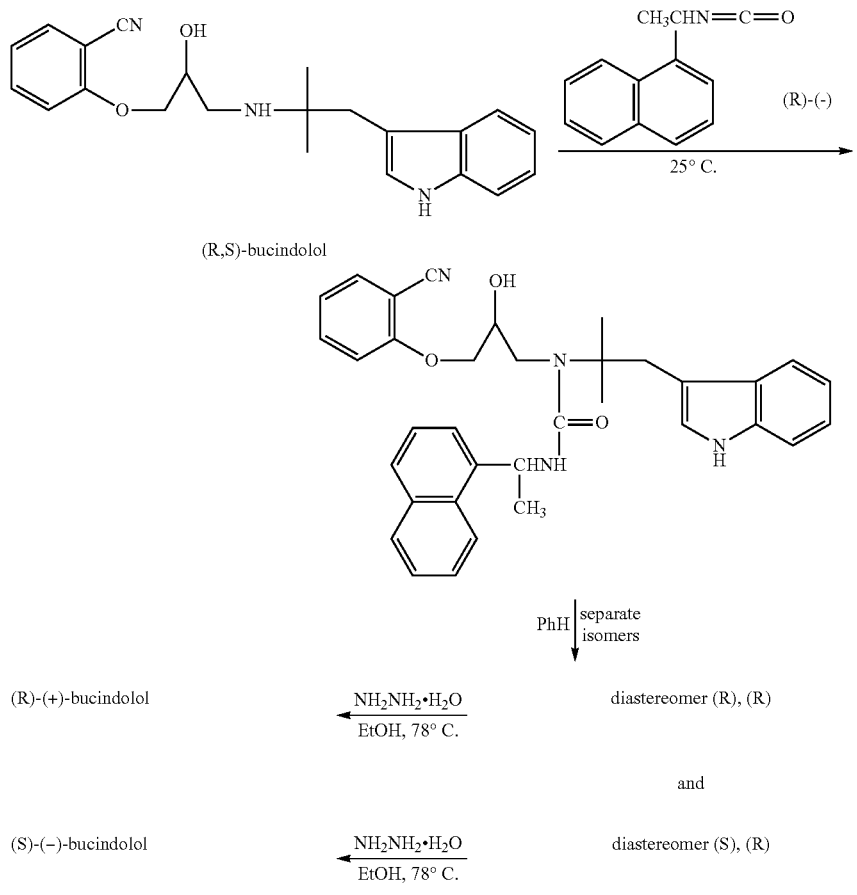

SCHEME 1

Preparation of Solutions

Note: Prepare solutions in sufficient quantities to meet the needs of the analysis. use appropriate proportions of solutions to maintain the ratio of the final solution.

Mobile Phase

Add 1 mL of diethylamine (DEA) to every 500 mL of ethanol. Mix, filter, and degas under vacuum with sonication.

System Suitability Solution

Accurately weight 25±1 mg of (R)-bucindolol and 25±1 mg of (S)-bucindolol into the same 100 mL volumetric flask and dissolve in mobile phase. Transfer 3 mL to a 10 mL volumetric flask and dilute to volume with mobile phase.

Alternatively, weigh approximately 50 mg of racemic bucindolol HCl reference standard into a 100 mL volumetric flask and prepare as above.

Preparation of Samples

Prepare these solutions in duplicate.

Preparation of Drug Substance Samples

Accurately weigh 25±1 mg of the drug substance sample into a 50 mL volumetric flask and dissolve in mobile phase. Transfer 3 mL to a 10 mL volumetric flask and dilute to volume with mobile phase. Transfer the 10 mL aliquot to a disposable syringe that is fitted with an 0.2 µm filter. Spend the first 2 mL to waste and collect the remaining portion for analysis.

Preparation of Tablet Samples

Accurately weigh 20 tablets individually and determine the average tablet weight. Grind the tablets as a composite. From the composite, accurately weigh the equivalent of one tablet into an appropriate volumetric flask (V1 in Table 1). Dilute to volume with mobile phase and sonicate for 5 minutes. Transfer (T1) mL to an appropriate volumetric flask (V2) and dilute to volume with mobile phase (no further dilution is required for some doses, as indicated by NA in the table). Transfer 10 mL of the final solution to a disposable syringe that is fitted with an 0.2 µm filter. Spend the first 2 mL to waste and collect the remaining portion for analysis.

TABLE 1

| Dose (mg) | Initial Volume (V1) (mL) | Transfer Volume (T1) (mL) | Final Volume (V2) (mL) |
|---|---|---|---|
| 3.0 | 25 | NA | NA |
| 6.25 | 50 | NA | NA |
| 12.5 | 100 | NA | NA |
| 25.0 | 50 | 6 | 25 |
| 50.0 | 100 | 6 | 25 |
| 100 | 250 | 3 | 10 |

Preparation of Capsule Samples

Empty the contents of 20 capsules into a vial and mix to obtain a composite. From the composite, accurately weigh 500 mg into an appropriate volumetric flask (V1 in Table 2). Dilute to volume with mobile phase and sonicate for 5 minutes. Transfer (T1) mL to an appropriate volumetric flask (V2) and dilute to volume with mobile phase (no further dilution is required for some doses, as indicated by NA in the table). Transfer 10 mL of the final solution to a disposable syringe that is fitted with an 0.2 µm filter. Spend the first 2 mL to waste and collect the remaining portion for analysis.

TABLE 2

| Dose (mg) | Initial Volume (V1) (mL) | Transfer Volume (T1) (mL) | Final Volume (V2) (mL) |
|---|---|---|---|
| 3.0 | 25 | NA | NA |
| 6.25 | 50 | NA | NA |
| 12.5 | 100 | NA | NA |
| 25.0 | 50 | 6 | 25 |
| 50.0 | 100 | 6 | 25 |
| 100 | 250 | 3 | 10 |

Chromatographic Conditions

| | |
|---|---|
| Column | Chiralpak AD (4.6 mm id × 25 cm) |
| Column temperature | ambient |
| Autosampler Tray Temp. | ambient |
| Mobile Phase | See section Mobile Phase |
| Flow rate | 0.5 mL/min |
| Needle Wash | Mobile Phase section |
| Injection Volume | 10 µL |
| Injections per vial | 2 |
| Wavelength | 220 nm |
| Run time | 15 min (may be adjusted as appropriate) |

System Suitability

System Interferences

Perform duplicate injections of mobile phase as a blank. No interfering peaks or artifacts should be present in the blank chromatograms Relative Retention Times Perform duplication injections of the system suitability solution. Using the second injection, report the relative retention times of each bucindolol peak. The relative retention times of (R)- and (S)-bucindolol should be approximately 1.00 and 1.23, respectively.

Peak Tailing

Using the same injection as for Relative Retention Times above, calculate the tailing factors for both bucindolol peaks as follows:

$$T = \frac{W}{2 \times F}$$

where:

T=tailing factor

W=peak width at 5% of peak height

F=width of line from peak start to the retention time at 5% of peak height

The tailing factors for both peaks should be ≤1.5

System Suitability

Perform duplicate injections of each sample.

Calculations

For all substance and product samples, calculate the percent (R)- and percent (S)-bucindolol as follows:

% (R)-bucindolol=(peak area(R)×100%/(peak area (R)+peak area(S))

% (S)-bucindolol=(peak area(S)×100%/(peak area(R)+ peak area(S))

Example 5

Preparations of (S)-bucindolol

Reaction 1.

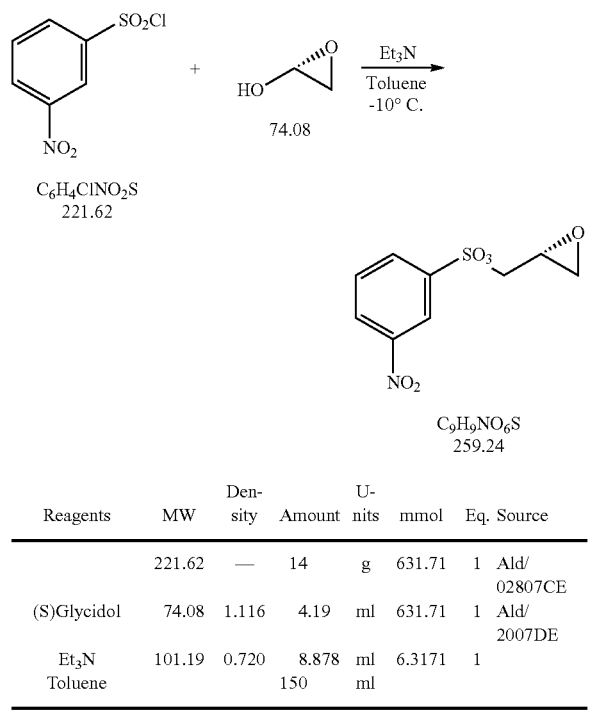

C₉H₉NO₆S
259.24

| Reagents | MW | Density | Amount | Units | mmol | Eq. | Source |
|---|---|---|---|---|---|---|---|
|  | 221.62 | — | 14 | g | 631.71 | 1 | Ald/02807CE |
| (S)Glycidol | 74.08 | 1.116 | 4.19 | ml | 631.71 | 1 | Ald/2007DE |
| Et₃N | 101.19 | 0.720 | 8.878 | ml | 6.3171 | 1 |  |
| Toluene |  |  | 150 | ml |  |  |  |

Procedure:

To a round-bottom flask 4.19 ml (S)-glycidol, 8.878 ml of Et₃N and 150 ml of Toluene was added. The reaction mixture was stirred in a N₂ atm. The reaction mixture was cooled to −10° C. Then Nitrosulfaryl chloride was added in 3 lots. The reaction mixture was stirred for two hours. After the completion of the reaction, water was added to the reaction mixture. The compound was taken up in EtOAc. The EtOAc layer was washed with brine. The EtOAc layer was dried and concentrated. The compound was purified by column chromatography.

Theoretical Yield: 16.376 g

% Yield: 93%

Yield obtained: 15.140 g

¹H NMR: verified

Reaction 2.

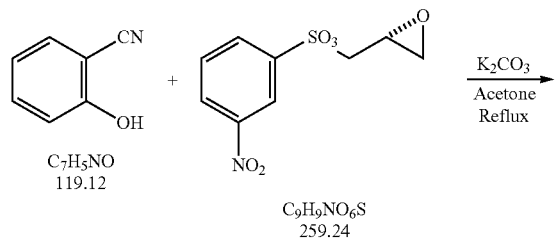

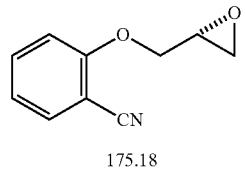

175.18

| Reagents | MW | Density | Amount | Units | mmol | Eq. |
|---|---|---|---|---|---|---|
| 2-Cyanophenol | 119.12 | — | 1 | g | 8.394 | 1 |
| Nolylate | 259.24 | — | 2.17 | g | 8.394 | 1 |
| K₂CO₃ | 138.21 | — | 3.48 | g | 25.182 | 3 |
| acetone (HPLC grade) |  |  | 50 | ml |  |  |

Procedure:

2-Cyanophenol was taken up in acetone. To that K₂CO₃ was added. The reaction mixture was refluxed for 30 min. Then the reaction mixture was cooled to room temperature. Nolylate was added and again refluxed. The reaction was monitored by HPLC. After the completion of the reaction, K₂CO₃ was then filtered/removed using scintered glass crucible. The filtrate was concentrated and purified by column chromatography (30% EtOAc in hexanes).

Theoretical Yield: 1.470 g

Yield Obtained: 1.4 g

¹H NMR: verified

Reaction 3.

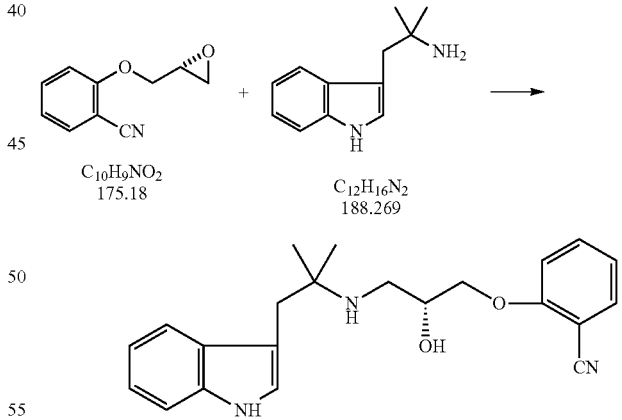

| Reagents | MW | Density | Amount | Units | mmol | Eq. |
|---|---|---|---|---|---|---|
| Expoxide | 175.18 | — | 7 | g | 39.958 | 1 |
| Amine | 188.269 | — | 7.52 | g | 39.958 | 1 |
| Ethanol |  |  | 125 | ml |  |  |

Procedure:

Epoxide and amine dissolved in EtOH and refluxed. After the completion of the reaction, the ethanol was removed. The residue was purified by column chromatography.

Theoretical Yield: 14.52 g

Yield Obtained: 5.5 g, HPLC purity 100% (1$^{st}$ reaction)

6.5 g HPLC purity 98% (2$^{nd}$ reaction)

$^{1}$H NMR: verified for both

Reaction 4.

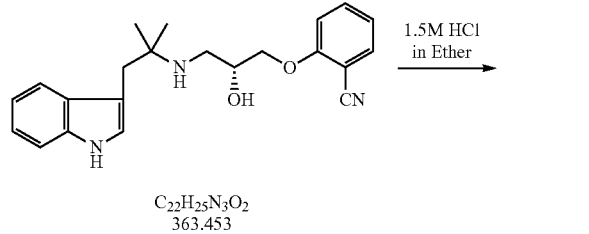 [SMILES: CC(C)(Cc1c[nH]c2ccccc12)NC[C@@H](O)COc1ccccc1C#N]

$C_{22}H_{25}N_3O_2$
363.453

S enantiomer
$C_{22}H_{27}N_3O_2Cl$
400.92

| Reagents | MW | Density | Amount | Units | mmol | Eq. |
|---|---|---|---|---|---|---|
| SM | 363.45 | — | 5.5 | g | 15.132 | 1 |
| HCl in ether | 1.5M | | 10.08 | ml | 15.132 | 1 |
| Diethyl ether | | | 50 | ml | | |

Procedure:

The starting material was dissolved in diethyl ether and to that 1.5 M HCl was added and allowed to stir for 2 hours. After that diethyl ether was removed. The resulting solid was dried.

Theoretical Yield: 6.06 g

Yield Obtained: 5.750 g

% Yield: 95%

Chiral HPLC purity: 100%

HPLC purity: 99%

$^{1}$H NMR: verified

Reaction 5.

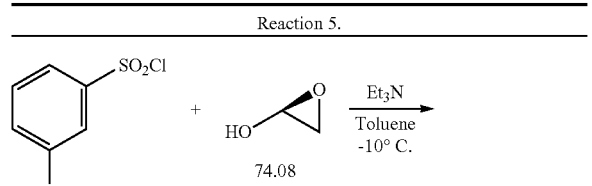

$C_6H_4ClNO_2S$
221.62

74.08
R-glycidol

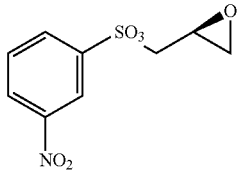

$C_9H_9NO_6S$
259.24

| Reagents | MW | Density | Amount | Units | mmol | Eq. | Source |
|---|---|---|---|---|---|---|---|
| | 221.62 | — | 15 | g | 67.683 | 1 | Ald/12007DE |
| R-glycidol | 74.08 | 1.116 | 4.49 | ml | 67.683 | 1 | Ald/02020BH |
| Et$_3$N | 101.19 | 0.720 | 9.512 | ml | 67.683 | 1 | |
| Toluene | | | | | | | |

Procedure: As in IN-SPL-C-11

To R-glycidol, toluene and Et$_3$N were added. Then Nitrosulfonyl chloride was added in lots at −10° C. and stirred for 2 hours. Following EtOAc/water work up, the residue was purified by column chromatography.

Theoretical Yield: 17.54 g

Yield Obtained: 15.5 g

% Yield: 88%

$^{1}$H NMR: verified

Reaction 6.

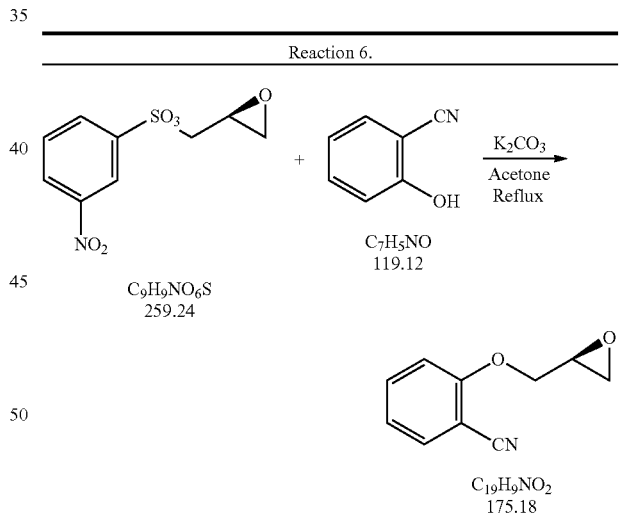

$C_9H_9NO_6S$
259.24

$C_7H_5NO$
119.12

$C_{19}H_9NO_2$
175.18

| Reagents | MW | Density | Amount | Units | mmol | Eq. | Source |
|---|---|---|---|---|---|---|---|
| 2-Cyanophenol | 119.12 | — | 6.89 | g | 57.86 | 1 | AM R1/290328 |
| Nolylate | 259.24 | — | 15.0 | g | 57.86 | 1 | |
| K$_2$CO$_3$ | 138.21 | — | 23.9 | g | 173.58 | 3 | |
| Acetone | | | 200 | ml | | | |

Procedure:

2-Cyanophenol in acetone and K$_2$CO$_3$ were heated at reflux for 30 min. Then cooled Nolylate was added and heated to reflux. As in Reaction 2, the reaction was monitored by HPLC. After the completion of the reaction K₂CO₃ filtered/removed. The filtrate was concentrated and purified by column chromatography.

Theoretical Yield: 10.13 g

Yield Obtained: 7.3 g

% Yield: 72%

¹H NMR: verified

---

Reaction 7.

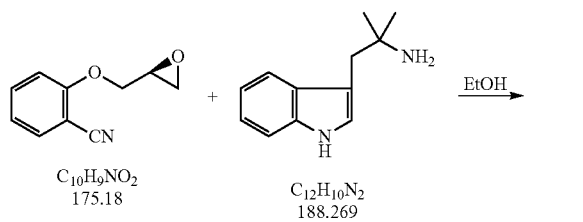

| Reagents | MW | Density | Amount | Units | mmol | Eq. |
|---|---|---|---|---|---|---|
| Epoxide | 175.18 | — | 7 | g | 39.958 | 1 |
| Amine | 188.269 | — | 7.52 | g | 39.958 | 1 |
| Ethanol | | | 150 | ml | | |

Procedure:

The Epoxide and amine, each in Ethanol, were heated to reflux. Then Ethanol was removed after the completion of reaction and purified by column chromatography.

Theoretical Yield: 14.523 g

Yield Obtained: 10.5 g

% Yield: 72%

---

Reaction 8.

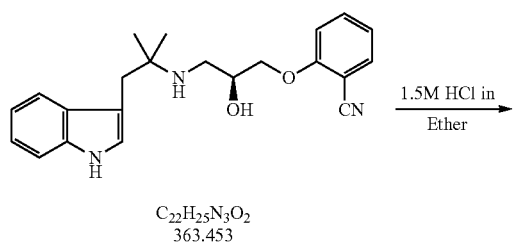 [SMILES: CC(C)(Cc1c[nH]c2ccccc12)NC[C@H](O)COc1ccccc1C#N]

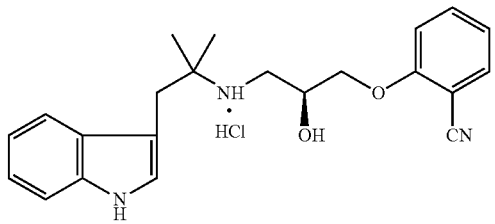

| Reagents | MW | Density | Amount | Units | mmol | Eq. |
|---|---|---|---|---|---|---|
| Starting material | 363.453 | — | 10 | g | 27.51 | 1 |
| HCl in Ether | 1.5M | | 18.34 | ml | 27.51 | 1 |
| Diethyl ether | | | 200 | ml | | |

Procedure:

Starting material was dissolved in diethyl ether. To that 1.5 M HCl was added and allowed to stir for 2 hours. Then ether was removed. The resulting solid was dried.

Theoretical Yield: 11.030 g

Yield Obtained: 10.5 g

% Yield: 95%

Chiral HPLC purity: 100%

HPLC Purity: 99%

¹H NMR: verified

Example 6

Characterization Data of (R)- and (S)-Bucindolol

Figure 15:
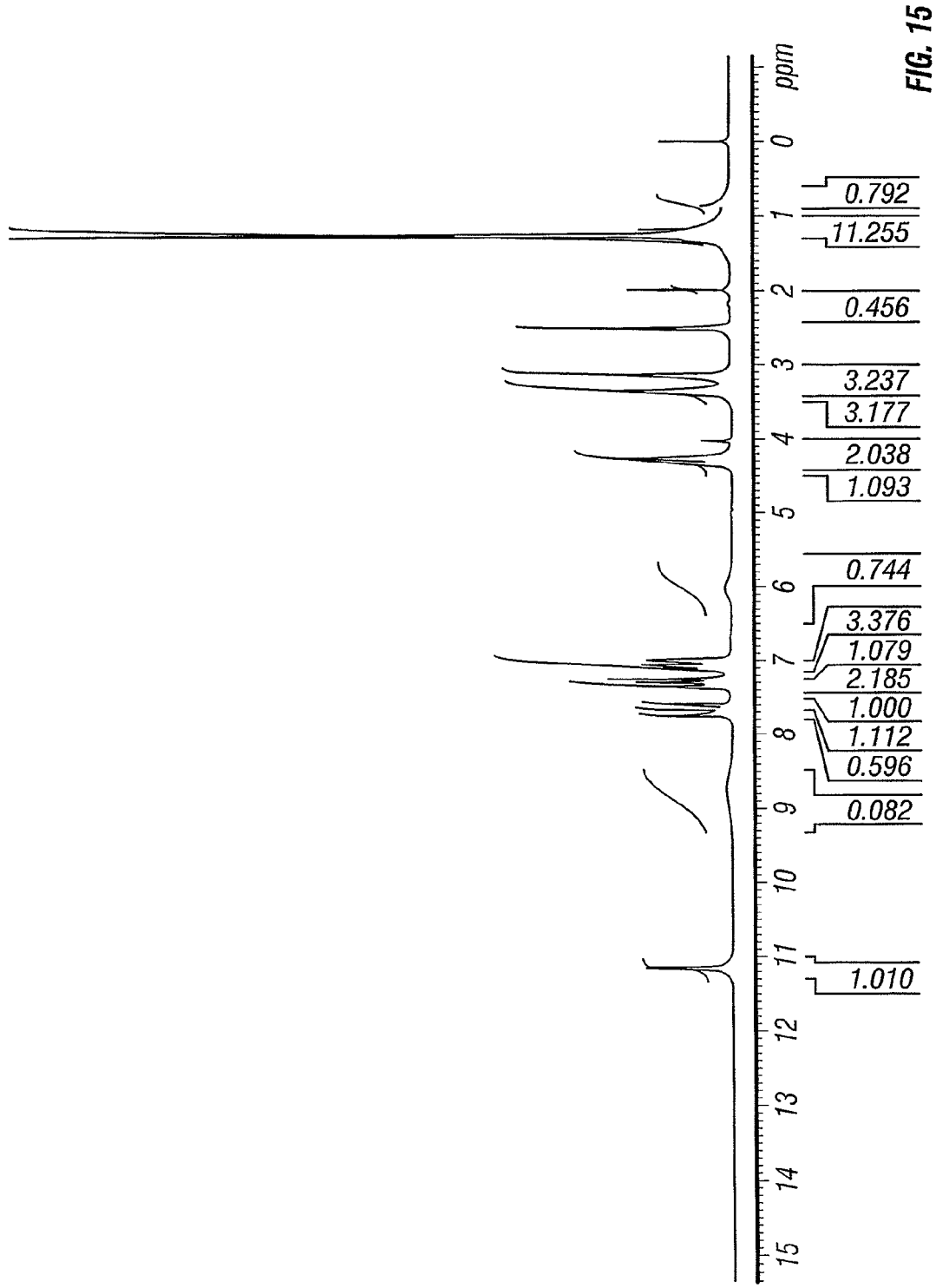
FIG. 15. ¹H NMR spectrum of (R)-bucindolol (sample in DMSO-$d_6$); 300 MHz.
Figure 16:
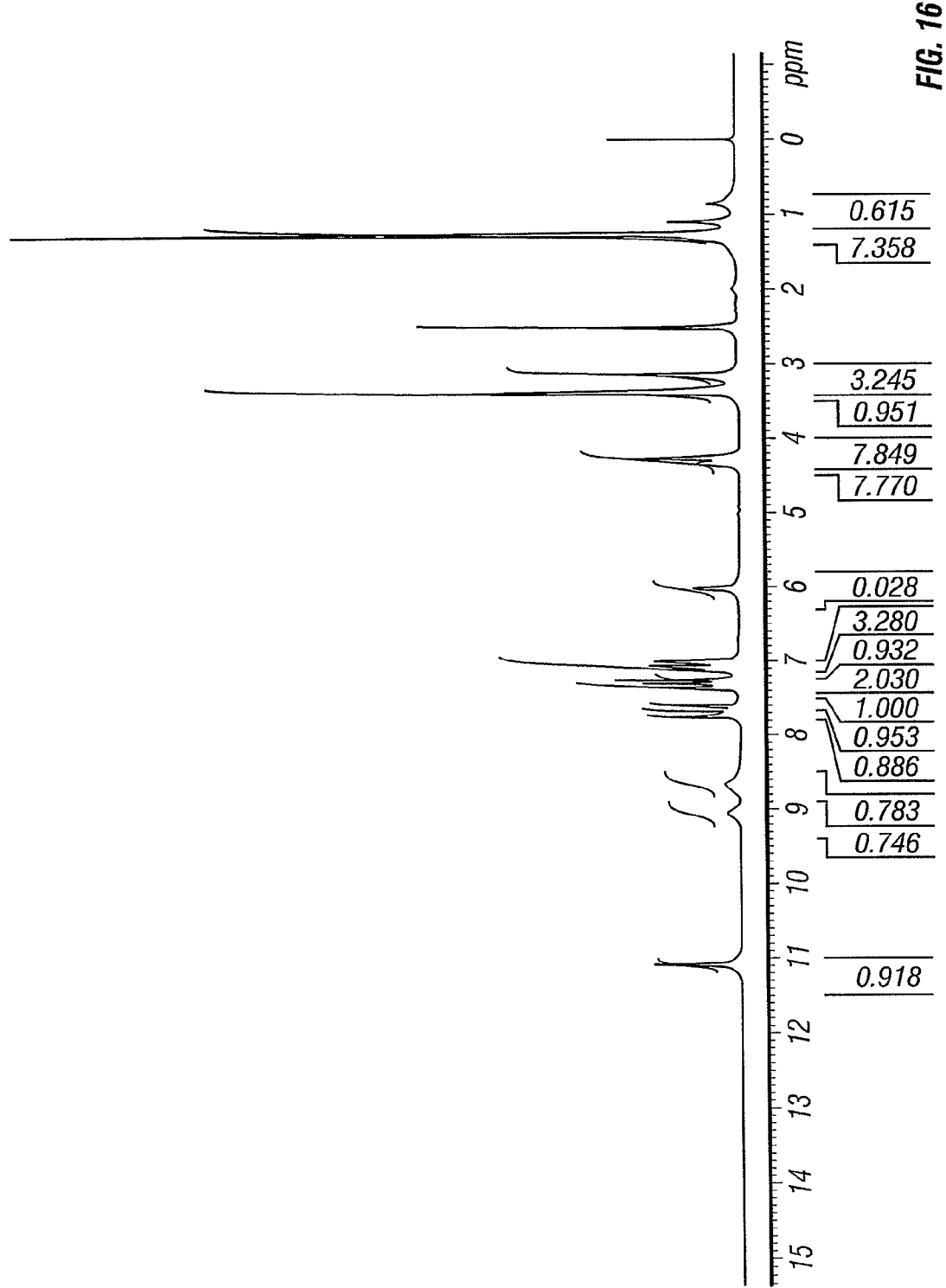
FIG. 16. ¹H NMR spectrum of (S)-bucindolol (sample in DMSO-$d_6$); 300 MHz.

See FIGS. 15 and 16 for ¹H NMR spectra of (R)- and (S)-bucindolol.

(R)-Bucindolol:

| TEST | RESULT/REFERENCE |
|---|---|
| Appearance | Light green solid |
| 300 MHz ¹H NMR Spectrum (DMSO-d₆) | Consistent - Attached |
| Mass Spectrum | ESI, m/z 364 [M + H]⁺, Attached |
| Chiral HPLC Analysis | >99% (area %), >99% ee, CHIRALPAK AD Column, Detector @ 280 nm, Attached |
| Optical Rotation | [α]²²·⁹_D + 15.5° (c 1.00, Methanol) |

(S)-Bucindolol

| TEST | RESULT/REFERENCE |
|---|---|
| Appearance | White solid |
| 300 MHz ¹H NMR Spectrum (DMSO-d₆) | Consistent - Attached |
| Mass Spectrum | ESI, m/z 364 [M + H]⁺, Attached |
| Chiral HPLC Analysis | >99% (area %), >99% ee, CHIRALPAK AD Column, Detector @ 280 nm, Attached |
| Optical Rotation | [α]²²·⁷_D − 15.9° (c 1.00, Methanol) |

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 7,396,829
U.S. Pat. No. 7,348,319
U.S. Pat. No. 7,155,284
U.S. Pat. No. 7,138,430
U.S. Pat. No. 7,052,695
U.S. Pat. No. 6,358,536
U.S. Pat. No. 5,208,233
Aguilar-Salinas et al., *Diabetes Care*, 26:2021-2026, 2003.
Aguilar-Salinas et al., *J. Lipid. Res.*, 42:1298-1307, 2001.
Campia et al., *J. Am. Coll. Cardiol.*, 40:754-760, 2002.
Danilewicz and Kemp, *J. Med. Chem.*, 16:168, 1973.
Gryglewski et al., *Nature*, 320:454-456, 1986.
Harrison et al., *Circ. Res.*, 61:74-80, 1987.
Harrison, *J. Clin. Invest.*, 100:2153-2157, 1997.
Huerta-Vazquez et al., *Arterioscler. Thromb. Vasc. Biol.*, 25:1985-1991, 2005.
Hunt et al., *Diabetes Care*, 26:1557-1563, 2002.
Kalinowski et al., *Circulation*, 109:2511-2517, 2004.
Kolomiets et al., *Chem. Abstr.*, 16(5):976, 1980.
Liao, *Clin. Chem.*, 44:1799-1808, 1998.
Liggett et al., *Proc Natl Acad Sci USA.*, 103:11288-11293, 2006.
Lvovich and Scheeline, *Anal. Chem.*, 69:454-462, 1997.
Malinski and Taha, *Nature*, 358(6388):676-678, 1992.
Oemar et al., *Circulation*, 97(25):2494-2498, 1998.
Paniagua et al., *Circulation*, 103:1752-1758, 2001.
Panza et al., *N. Engl. J. Med.*, 323:22-27, 1990.
Pirkle and Hoekstra, *J. Org. Chem.*, 39:3904, 1984.
Pirkle and Hauske, *J. Org. Chem.*, 42:1839, 1977a.
Pirkle and Hauske, *J. Org. Chem.*, 42:2781, 1977b
Stein et al., *Clin. Pharmacol. Ther.*, 62:436-443, 1997.
Stern et al., *Diabetes Care*, 14:649-654, 1991.
Taddei et al., *Hypertension*, 21:929-933, 1993.
Walsh et al., *J Cardiac Failure*, 14(6):S8, 2008.
Zou et al., *J. Clin. Invest.*, 109:817-826, 2002.

The invention claimed is:

1. A pharmaceutical composition comprising a pharmaceutically acceptable carrier and bucindolol substantially free of its R-stereoisomer and an additional pharmaceutical agent, wherein the additional pharmaceutical agent is a nitric oxide (NO) enhancing agent.

2. The pharmaceutical composition of claim 1, wherein the ratio of S-bucindolol to R-bucindolol in the composition is at least about 80:20 by weight.

3. The pharmaceutical composition of claim 2, wherein the ratio of S-bucindolol to R-bucindolol in the composition is at least about 90:10 by weight.

4. The pharmaceutical composition of claim 3, wherein the ratio of S-bucindolol to R-bucindolol in the composition is at least about 99:1 by weight.

5. The pharmaceutical composition of claim 1, wherein the composition further comprises a second additional pharmaceutical agent, wherein the second additional pharmaceutical agent treats a symptom or condition related to a cardiovascular disease, a neurological disease, an infectious disease, an inflammatory disease, a neoplasm, a gastrointestinal disease, a genitourinary disease, a pulmonary disease, or an immune disease.

6. The pharmaceutical composition of claim 5, wherein the second additional pharmaceutical agent comprises a beta-adrenergic receptor blocker.

7. The pharmaceutical composition of claim 1, wherein the NO enhancing agent is a RAS inhibitor, a statin, a PDE5 inhibitor, a NO-conjugated drug, or a diazeniumdiolate.

8. The pharmaceutical composition of claim 7, wherein the NO enhancing agent is a statin.

9. The pharmaceutical composition of claim 8, wherein the statin is atorvastatin, fluvastatin, lovastatin, pravastatin, rosuvastatin calcium, and simvastatin.

10. A method of treating a patient comprising administering to said patient a therapeutically effective amount of a composition comprising bucindolol, wherein the composition is substantially free of the R-stereoisomer of bucindolol, wherein the patient exhibits the symptoms of or been diagnosed with a right ventricular heart failure, congestive heart failure, hypertension, angina, myocardial infarction, or cardiac arrhythmia and wherein the patient is a human and the composition comprises a dose of 40 mg to 200 mg of bucindolol, the dose being prescribed to be administered at least once daily over a period of at least 28 days.

11. The method of claim 10, wherein the patient is in need of a beta-blocker.

12. The method of claim 11, wherein the patient has exhibited the symptoms of or been diagnosed with mitral valve prolapse, hypertrophic obstructive cardiomyopathy, or acute dissecting aortic aneurysm.

13. The method of claim 10, wherein the ratio of S-bucindolol to R-bucindolol in the composition is at least 80:20 by weight.

14. The method of claim 13, wherein the ratio of S-bucindolol to R-bucindolol in the composition is at least 90:10 by weight.

15. The method of claim 14, wherein the ratio of S-bucindolol to R-bucindolol in the composition is at least 99:1 by weight.

16. The method of claim 10, wherein bucindolol is in a solid form.

17. The method of claim 16, wherein the composition is administered twice daily.

18. The method of claim 17, wherein the composition is administered orally.

19. The method of claim 10, wherein the composition comprises 50 mg to 100 mg of bucindolol.

20. The bucindolol of claim 1, wherein the bucindolol is in a salt form.

21. An oral pharmaceutical composition comprising a pharmaceutically acceptable carrier and bucindolol substantially free of its R-stereoisomer and an additional pharmaceutical agent, wherein the additional pharmaceutical agent is a beta-adrenergic receptor blocker.

* * * * *